United States Patent
Nguyen et al.

(10) Patent No.: US 12,426,904 B2
(45) Date of Patent: Sep. 30, 2025

(54) INTRAVASCULAR LITHOTRIPSY CATHETER WITH OSCILLATING IMPACTOR

(71) Applicant: Shockwave Medical, Inc., Santa Clara, CA (US)

(72) Inventors: Hoa D. Nguyen, San Jose, CA (US); Patrick Stephens, Santa Clara, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 0 days.

(21) Appl. No.: 18/513,421

(22) Filed: Nov. 17, 2023

(65) Prior Publication Data
US 2025/0160864 A1   May 22, 2025

(51) Int. Cl.
*A61B 17/22* (2006.01)

(52) U.S. Cl.
CPC .... *A61B 17/2202* (2013.01); *A61B 17/22022* (2013.01); *A61B 2017/22021* (2013.01); *A61B 2017/22024* (2013.01); *A61B 2017/22025* (2013.01); *A61B 2217/007* (2013.01); *A61B 2560/04* (2013.01)

(58) Field of Classification Search
CPC .......... A61B 17/2202; A61B 17/22022; A61B 2017/22021; A61B 2017/22024; A61B 2017/22025; A61B 2560/04; A61B 17/225; A61B 2017/22051
See application file for complete search history.

(56) References Cited

U.S. PATENT DOCUMENTS

| | | | |
|---|---|---|---|
| 2,916,647 | A | 12/1959 | George |
| 3,412,288 | A | 11/1968 | Ostrander |
| 3,413,976 | A | 12/1968 | Roze |
| 3,524,101 | A | 8/1970 | Barbini |
| 3,583,766 | A | 6/1971 | Padberg |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

International Search Report and Written Opinion received for International Patent Application No. PCT/US2023/080410, mailed on Aug. 6, 2024, 9 pages.

*Primary Examiner* — Brigid K Byrd
(74) *Attorney, Agent, or Firm* — Morrison & Foerster LLP

(57) ABSTRACT

Catheter devices for treating occlusions in body lumen are described herein. The catheter devices may include a tubular body having a distal end, an distal portion elastically connected to the distal end of the tubular body, an impactor connected to the distal portion and separated by a space from the distal end of the tubular body, a distal shock wave emitter located adjacent to the space and connected to a power source, and an enclosure at least partially surrounding each of the distal end of the tubular body, the elastic distal portion, the impactor, and the distal shock wave emitter. The impactor may be configured to move in response to shock waves generated from the distal shock wave emitter, such that a length of the space in the proximal-distal direction increases by between 0.05 mm and 0.6 mm.

26 Claims, 15 Drawing Sheets

(56) References Cited

U.S. PATENT DOCUMENTS

| | | |
|---|---|---|
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A * | 1/1994 | Rosen ............. A61B 17/22022 606/15 |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A * | 6/1995 | Rosen .................... A61B 18/26 604/164.08 |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,765,440 B2 | 9/2020 | Tozzi |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |

(56) References Cited

U.S. PATENT DOCUMENTS

| | | |
|---|---|---|
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0142754 A1* | 6/2006 | Irion ............... A61B 17/22022 606/41 |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2008/0191596 A1* | 8/2008 | King ............... G10K 15/06 313/165 |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0214061 A1 | 7/2014 | Adams et al. |
| 2015/0157399 A1 | 6/2015 | Romoscanu |
| 2015/0320432 A1 | 11/2015 | Adams |
| 2016/0151081 A1 | 6/2016 | Adams et al. |
| 2016/0262784 A1* | 9/2016 | Grace ............... A61B 17/22022 |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2017/0360461 A1* | 12/2017 | Dolgin ............... A61B 17/2202 |
| 2019/0150960 A1 | 5/2019 | Nguyen et al. |
| 2019/0388110 A1 | 12/2019 | Nguyen et al. |
| 2020/0306512 A1* | 10/2020 | Bahmanyar ...... A61B 17/22012 |
| 2021/0085347 A1* | 3/2021 | Phan ................ A61B 17/22004 |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0107690 A1 | 4/2023 | Nguyen |
| 2023/0123003 A1 | 4/2023 | Vo |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |
| JP | 2011524203 A | 9/2011 |

(56) References Cited

FOREIGN PATENT DOCUMENTS

| | | |
|---|---|---|
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 5/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2018236551 A1 | 12/2018 |
| WO | WO-2019099218 A1 | 5/2019 |

\* cited by examiner

INTRAVASCULAR LITHOTRIPSY CATHETER WITH OSCILLATING IMPACTOR

FIELD OF THE DISCLOSURE

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to inflate in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the power source used to generate the acoustic shock waves, with two exemplary power sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential power sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guide wire through a patient's vasculature until it is positioned proximal to and/or aligned with a calcified plaque lesion in a body lumen. The balloon is then inflated with conductive fluid (using a relatively low pressure of 2-4 atm) so that the balloon inflates to contact the lesion, but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be inflated further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

When treating occlusions, a physician must first cross the occlusion (e.g., pass through the occluded area), and then feed the angioplasty balloon and/or other tools down the artery to the blockage to perform the desired procedure. In some instances, however, such as the case of a chronic total occlusion ("CTO"), the occlusion may be so tight and solid that it is difficult to cross the treatment device into the true lumen of the distal vessel. Conventional guide wires may have difficulty penetrating the thick, fibrous caps of CTOs, and may risk trauma to blood vessels when navigating narrow and tortuous regions of vasculature. Some physicians may implement atherectomy procedures (e.g., laser-based, mechanically cutting or shaving, mechanically rotating devices, etc.) to form a channel in a CTO in combination with an angioplasty balloon treatment, but many atherectomy devices and systems carry a higher risk of vessel perforation or vessel dissection as compared with a basic angioplasty balloon catheters. Even if the initial puncture of a CTO is successful, placement of dilation devices, like angioplasty balloons, can be very difficult in chronically occluded vessels. This makes the treatment of CTOs a technically challenging procedure that requires a long learning curve for interventional cardiologists. Accordingly, there is an unmet need for a device that can penetrate resistant fibrotic and calcified lesions, such as CTOs, while minimizing the risk of trauma to blood vessels. Similar devices are needed for treating occlusions formed in other parts of the body, for example, kidney stones in the urinary system.

SUMMARY

An IVL catheter that includes an impactor for delivering mechanical forces directly to occlusion in a body lumen and methods of using an IVL catheter that includes an impactor are described. In some designs, the impactor is attached to a distal end of a shock wave catheter that includes one or more emitters for generating shock waves. The impactor is a component for applying mechanical energy to occlusions by receiving shock wave energy and translating the shock wave energy into mechanical movement of the distal tip of the catheter. In various examples, the impactor may alternatively be referred to as a jackhammer, an awl, an auger, a gimlet and/or a proximal reciprocating member.

The impactor is oriented such that shock waves generated at one or more of the emitters impinge on the impactor causing the impactor to advance in a forward (i.e., distal) direction and then return to its original position. In this way, the distal end of the impactor can deliver a mechanical force to the occlusion by being driven into the occlusion by the shock waves. Repeated generation of shock waves can cause the impactor to oscillate forward and backward and produces a "jackhammer effect" that can chisel away at the CTO calcium and create a tunnel to advance the catheter forward. Once the catheter tip enters the tunnel, in some embodiments radial shock waves can be used to crack calcium in the body lumen and make the lesion pliable. Such devices may be useful for treating occlusions in body lumens, such as CTOs in vasculature, without risking harm to the lumen wall.

In some examples, a catheter for treating an occlusion in a body lumen is provided. The catheter includes a hollow tubular body including a distal portion configured to move relative to a proximal portion of the hollow tubular body. The catheter further includes a conductor configured to receive a voltage pulse from a voltage source. The catheter further includes an impactor mounted on the distal portion of the hollow tubular body, the impactor comprising a conductive portion adjacent to a distal end of the pair of conductor. When a voltage pulse is applied to the conductor, current flows across a gap between the conductor and the conductive portion to generate one or more shock waves that cause the impactor to move in a distal direction.

In some examples, when the impactor moves in the distal direction, the distal portion of the hollow tubular body moves in conjunction with the impactor. In some examples, the impactor and the distal portion move in the distal direction with respect to the proximal portion of the hollow tubular body. In some examples, the distal portion is elastically coupled to the proximal portion. In some examples, the distal portion comprises bellows that increase a length of the distal portion when the impactor moves in the distal direction. In some examples, the impactor moves in a distal direction less than 0.5 mm with respect to the proximal portion of the hollow tubular body. In some examples, the impactor comprises a conductive metal sheath. In some examples, the impactor tapers from a proximal end of the impactor to a distal end of the impactor. In some examples, the conductive portion of the impactor comprises a first conductive portion and a second conductive portion. In some examples, the first conductive portion of the impactor comprises a first cut-out in a proximal edge of the impactor, and the second conductive portion of the impactor comprises a second cut-out in the proximal edge of the impactor.

In some examples, the catheter further includes an enclosure surrounding at least a portion of the hollow tubular body. In some examples, a proximal end of the enclosure is sealed to the proximal portion of the hollow tubular body. In some examples, a distal end of the enclosure is sealed to the impactor. In some examples, the enclosure extends in length in conjunction with the advancement movement of the impactor. In some examples, the enclosure comprises bellows that increase a length of the enclosure when the impactor moves in the distal direction. In some examples, the hollow tubular body includes a first fluid lumen for flowing conductive fluid into the enclosure, the first fluid lumen having an outlet. In some examples, the hollow tubular body further includes a second fluid lumen for flowing conductive fluid out of the enclosure, the second fluid lumen having an inlet. In some examples, a path of fluid flow between the outlet and the inlet is across at least a portion of the conductive portions.

In some examples, the conductor forms a first electrode of a respective electrode pair, and a second electrode of the electrode pair is formed by the conductive portion of the impactor. In some examples, the conductor comprises a first pair of conductors. In some examples, the first pair of conductors includes a first insulated wire extending along a length of the hollow tubular body, the first insulated wire having an exposed distal tip spaced apart from a first conductive portion of the impactor at a first spark gap. In some examples, the first pair of conductors further includes a second insulated wire extending along the length of the hollow tubular body, the second insulated wire having an exposed distal tip spaced apart from a second conductive portion of the impactor at a second spark gap. In some examples, when a voltage pulse is applied across the first insulated wire and the second insulated wire, a current is configured to flow from the exposed distal tip of the first insulated wire to the first conductive portion across the first spark gap to generate a first shock wave, and wherein the current is further configured to flow from the second conductive portion to the exposed distal tip of the second insulated wire across the second spark gap to generate a second shock wave. In some examples, the catheter further includes a second pair of conductors configured to receive a voltage pulse from a voltage source, wherein, when a voltage pulse is applied to the second pair of conductors, current flows between the second pair of conductors and one or more proximal emitters to generate shock waves at one or more of the proximal emitters. In some examples, the catheter further includes a power source, wherein the power source is configured for selectively applying voltage pulses across either the first pair of conductors or the second pair of conductors.

In some examples, a method of treating an occlusion in a body lumen is provided. The method includes introducing a catheter into the body lumen. In some examples, the catheter includes a hollow tubular body comprising a distal portion configured to move relative to a proximal portion of the hollow tubular body; a conductor configured to receive a voltage pulse from a voltage source; and an impactor mounted on the distal portion of the hollow tubular body, the impactor comprising a conductive portion adjacent to a distal end of the conductor. The method further includes advancing the catheter within the body lumen such that a distal end of the impactor is positioned proximate to the occlusion. The method further includes applying a voltage pulse to the conductor such that current flows across a gap between the conductor and the conductive portion to generate one or more shock waves that cause the impactor to move in a distal direction.

In some examples, a catheter for treating an occlusion in a body lumen in provided. The catheter includes a tubular body having a distal end. The catheter further includes a distal portion elastically connected to the distal end of the tubular body. The catheter further includes an impactor connected to the distal portion and separated by a space from the distal end of the tubular body. The catheter further includes a distal shock wave emitter located adjacent to the space and connected to a power source by a wire. The catheter further includes an enclosure at least partially surrounding each of the distal end of the tubular body, the elastic distal portion, the impactor, and the distal shock wave emitter. In some examples, the impactor is configured to move in response to a shock wave generated from the distal shock wave emitter such that a length of the space in the proximal-distal direction increases by between 0.05 mm and 0.6 mm.

In some examples, a catheter for treating an occlusion in a body lumen is provided. The catheter includes a tubular body comprising a distal end. The catheter further includes a distal portion elastically connected to the distal end of the tubular body. The catheter further includes an impactor connected to the distal portion and configured to move in a distal-proximal direction. The catheter further includes a shock wave emitter located on or proximate the tubular body. The catheter further includes an enclosure surrounding the shock wave emitter and including a proximal region. The proximal region configured to expand in the distal-proximal direction in conjunction with distal movement of the impactor and further configured to contract in the distal-proximal direction in conjunction with proximal movement of the impactor. In some examples, the proximal region of the enclosure comprises proximal bellows. In some examples, the proximal region of the enclosure comprises pleats. In some examples, the proximal region is configured to expand in the distal-proximal direction responsive to shock waves generated at the shock wave emitter.

DESCRIPTION OF THE FIGURES

Illustrative aspects of the present disclosure are described in detail below with reference to the following figures. It is intended that the embodiments and figures disclosed herein are to be considered illustrative and exemplary rather than restrictive.

FIG. 2A illustrates the distal end an exemplary catheter having an impactor, where at least a portion of the impactor functions as a distal emitter. FIG. 2B illustrates the distal end of an exemplary catheter having an impactor, where at least a portion of the impactor functions as a distal emitter, along one or more proximal emitters disposed along a hollow tubular body of the catheter.

FIG. 5A illustrates a close-up perspective view of the distal end of an exemplary catheter showing an exemplary impactor. FIG. 5B illustrates an additional close-up perspective view of the exemplary catheter with the impactor removed.

FIG. 8A illustrates the impactor in a first position prior to the generation of a shock wave. FIG. 8B illustrates the impactor in a second position after advancing distally responsive to the generation of a shock wave. FIG. 8C illustrates a close up view of the distal end of the catheter to show a gap that forms between the impactor and the hollow tubular body after distal advancement of the impactor.

FIG. 9A illustrates an example of bellows that can be included in a distal portion of the catheter body. FIG. 9B illustrates exemplary bellows that can be included in an enclosure of a catheter. FIG. 9C illustrates an exemplary pleated region that can be included in an enclosure of a catheter.

DETAILED DESCRIPTION

Figure 1:
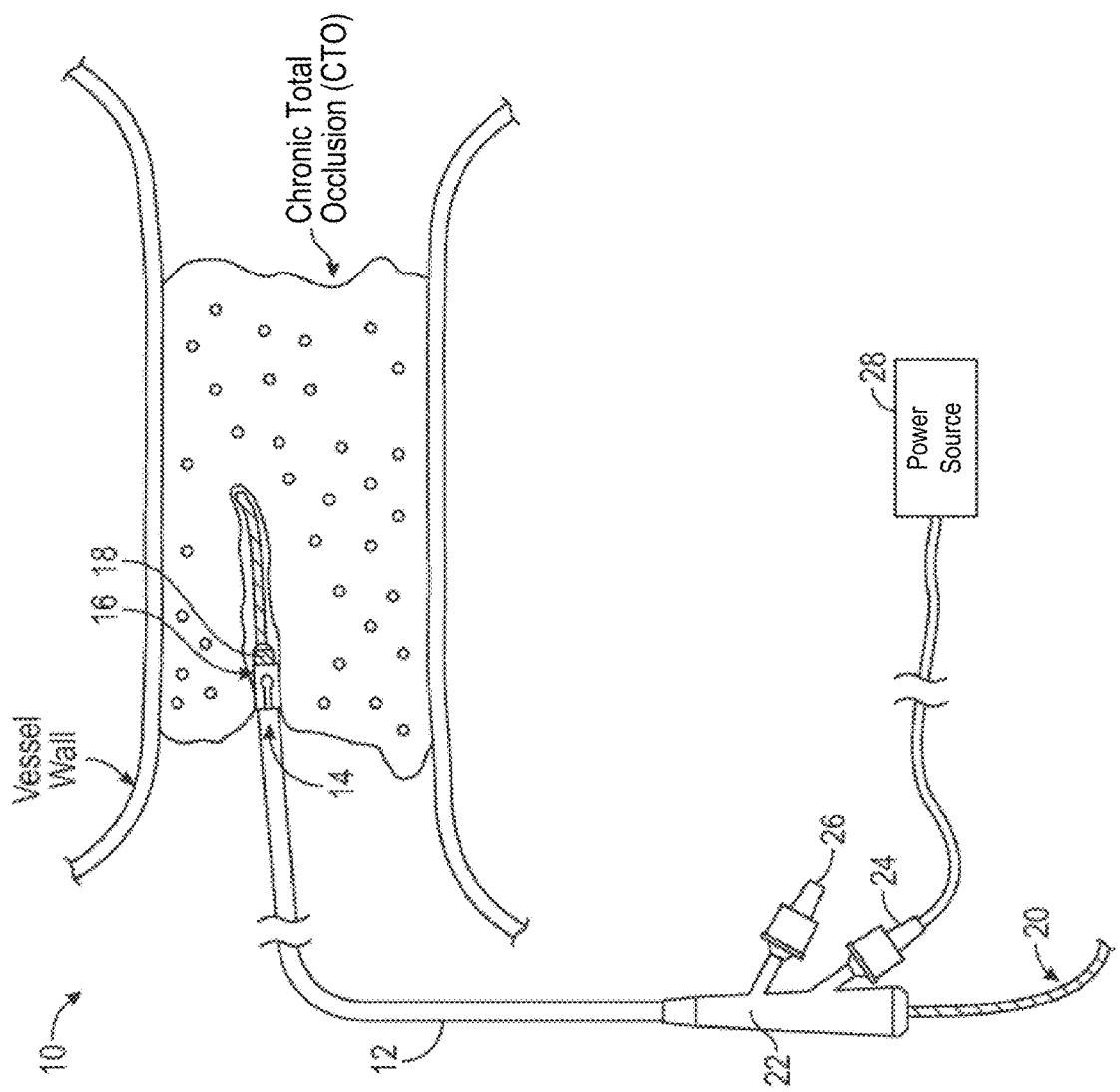
FIG. 1 illustrates an exemplary shock wave angioplasty catheter being used to treat a CTO in a blood vessel, according to one or more examples of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

The present disclosure relates generally to an IVL catheter system for treating occlusions in body lumens, such as CTOs, circumferential calcium, eccentric calcium, and/or other lesions in a patient's vasculature or kidney stones in a patient's ureter. Efforts have been made to improve the delivery of shock waves in catheter devices. For instance, forward-biased designs, such as the designs found in U.S. Pat. No. 10,966,737 and U.S. Publication No. 2019/0388110, both of which are incorporated herein by reference, direct shock waves in a generally forward direction (e.g., distally from the distal end of a catheter) to break up tighter and harder-to-cross occlusions in vasculature. Some catheter designs have changed the circumferential rotation (i.e., "clocking") or spacing of the emitters to direct shock wave energy in a particular direction and location relative to the catheter body and/or to increase constructive interference between the shock waves. Constructively interfering shock waves are described in U.S. Publication No. 2023/0123003, incorporated herein by reference. Some catheter devices have been designed to include arrays of low-profile electrode assemblies that reduce the crossing profile of the catheter and allow the catheter to more easily navigate calcified vessels to deliver shock waves in more severely occluded regions of vasculature. For instance, U.S. Pat. Nos. 8,888,788, and 10,709,462 and U.S. Publication No. 2021/0085347, each of which is incorporated herein by reference, provide examples of low-profile electrode assemblies. Such forward-biased and low-profile designs are particularly useful when an artery is totally or partially occluded, for example, with thrombus, plaque, fibrous plaque, and/or calcium deposits. Certain catheter devices have been designed with impactor elements that advance forward responsive to generated shockwaves to deliver mechanical forces directly to occlusions in vasculature. For instance, U.S. Publication No. 2023/0107690, incorporated herein by reference, provides an example of a shock wave catheter featuring an impactor.

The described catheter system may include one or more shock wave sources inside an enclosure for generating shock waves to treat an occlusion. The catheters of the present disclosure additionally include an impactor that, in response to the generation of shock waves, delivers mechanical forces to occlusions distal to the catheter. The impactor may be configured to move in a distal-proximal direction relative to a body of the catheter. The shock waves may impinge on the impactor to cause the impactor to accelerate in a distal direction and toward the occlusions distal to the catheter. After advancing forward to impact the occlusion, the impactor returns in a proximal direction to its original position. The impactor may be used to treat tighter and harder-to-cross lesions and CTOs than a catheter that does not include an impactor.

The impactor may be mounted to a distal portion of the catheter body with a distal end of the enclosure sealed to a region of the impactor. In some examples, the enclosure is sealed to the impactor such that a proximal end of the impactor is inside the enclosure, and a distal end of the impactor is outside of the enclosure. The distal end of the impactor may extend forward from the catheter body toward an occlusion such that the distal end can advance forward to mechanically impact an occlusion. In some examples, at least a portion of the impactor (e.g., at least a portion the impactor's proximal end) forms part of a distal emitter of the catheter and is configured for generating shock waves. For instance, the impactor may include one or more conductive portions (e.g., regions of conductive material) that serve as one or more electrodes of an electrode pair that functions as a distal emitter. One or more further electrodes of the electrode pair may be formed by a conductive portion of the catheter body, a conductive element disposed on the catheter body, or a conductive portion of a wire extending through the catheter body. However, other shock wave emitter configurations are also possible.

When a shock wave is generated at the distal emitter (which may be formed from a portion of the impactor and/or included near the distal end of the catheter proximal to the impactor), at least a portion of the shock wave energy impinges on the impactor causing the impactor to advance in a distal direction. When the impactor advances in the distal direction, the distal tip of the impactor advances in the body lumen to deliver a mechanical force directly to an occlusion. A distal portion of the catheter body (e.g., the portion of the catheter body on which the impactor is mounted) may be configured to advance in conjunction with the impactor. The catheter body may include features that permit the forward advancement of the impactor and the distal portion relative to a proximal portion of the catheter body, while the proximal portion remains stationary. For instance, in one example, the distal portion of the catheter body includes bellows (e.g., an accordion-shaped region of material) that extend the length of the distal portion to permit the distal advancement of the impactor and distal portion relative to the proximal portion. In another example, the distal portion of the catheter body is connected to the proximal portion by way of an elastomer (e.g., a region of elastic material) that can extend to permit the distal advancement of the impactor and the distal portion. In some examples, the enclosure of the catheter includes features that allow the enclosure to extend in length to allow for the advancement of the impactor and the distal end (e.g., bellows, pleats, or other features).

When the shock wave terminates, the distal portion of the catheter and the impactor return backward (i.e., in a proximal direction) to their original positions. In some examples, the return of the impactor and the distal portion in the proximal direction may be facilitated by the same features described above (e.g., the bellows, elastomer, or pleats). For instance, after the impactor and the distal portion have advanced in the distal direction, the bellows, elastomer, or pleats may impart a proximally directed spring-like force on the distal portion and the impactor to cause them to return in the proximal direction.

Generating repeated shock waves may cause the impactor to oscillate forward and backward, producing a "jackhammer effect" for clearing occlusions from a body lumen. Advantageously, incorporating an impactor that delivers direct mechanical forces to occlusions may enable the catheter to puncture and cross resistant and fibrous occlusions in body lumens that are difficult to treat through traditional angioplasty methods. Difficult to treat occlusions can include calcified and fibrotic tissues and CTOs.

In addition to impinging on the impactor to drive the impactor into occlusions distal to the catheter, at least a portion of the shock wave energy from the distal emitter may be transmitted (e.g., propagated) in a direction radial or transverse to the catheter. In some examples, one or more proximal emitters are provided for delivering shock wave energy in more proximal regions of the enclosure to treat lesions surrounding the catheter. This radially-directed shock wave energy propagates through walls of the enclosure to treat, e.g., calcified regions that have formed on walls of the body lumen. Paired with the impactor's forward-directed jackhammering, the transverse shock wave energy allows the catheter to continuously treat larger areas of an occluded vessel (e.g., both total occlusions distal to the catheter and calcified tissues surrounding the catheter) and may reduce the need for multiple devices during treatment of an occluded body lumen. Once a total occlusion has been disrupted (e.g., penetrated by the impactor to provide a space for entry of the distal end of the catheter body), the catheter may be advanced further into the body lumen and shock wave treatment can be continued.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to and spaced apart each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The terms "emitter sheath" and "emitter band" refers to a continuous or discontinuous band of conductive material that may form one or more electrodes of one or more electrode pairs, thereby forming a location of one or more emitters.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles. Accordingly, although some shock wave devices described herein generate shock waves based on high voltage pulses applied to electrodes, it should be understood that a shock wave device may additionally or alternatively use laser pulses transmitted through optical fibers to generate shock waves and that the "emitters", "electrodes", and "electrode pairs" described herein may instead include output ends of optical fibers. These examples are not intended to be a comprehensive list of potential power sources to create shock waves in shock wave catheters.

FIG. 1 illustrates an exemplary shock wave angioplasty catheter 10 being used to treat an occlusion in a blood vessel, such as a coronary chronic total occlusion (CTO), according to one or more aspects of the present disclosure. The catheter 10 is advanced into an occlusion in a patient's vasculature, such as the CTO depicted in FIG. 1, over a guide wire 20. A distal end 14 of the catheter 10 includes a shock wave generator 16 that produces shock waves at one or more emitters (e.g., electrode pairs) to break up occlusions. The distal end 14 further includes an impactor (not shown) that advances in a distal direction responsive to the generation of shock waves to deliver mechanical forces directly to the occlusion. When shock waves are generated at one or more of the emitters, the shock waves impinge on the impactor to drive the impactor forward and into the occlusion. Repeated shock waves cause the impactor to oscillate forward and backward with a "jackhammer effect" to help penetrate and clear occlusions from vasculature.

An enclosure 18 (e.g., a low-profile flexible angioplasty balloon, a polymer membrane in tension that can flex outward, etc.) is sealably attached to the distal end 14 of the catheter 10, forming an annular channel around the shaft 12 of the catheter. The enclosure 18 surrounds the shock wave generator 16, such that shock waves are produced in a closed system within the enclosure 18. The enclosure 18 can be filled with a conductive fluid, such as saline. The conductive fluid allows the acoustic shock waves to propagate outwardly from the electrode pairs of the shock wave generator 16 through the walls of the enclosure 18 and then into the target lesion. In one or more examples, the conductive fluid may also contain x-ray contrast fluid to permit fluoroscopic viewing of the catheter 10 during use.

The catheter 10 includes a proximal end 22 (or handle) that remains outside of a patient's vasculature during treatment. The proximal end 22 includes an entry port for receiving the guide wire 20. The proximal end 22 also includes a fluid port 26 for receiving a conductive fluid for filling and emptying the enclosure during treatment. A connection port 24 is located on the proximal end 22 to provide a connection between the distal shock wave generator 16 and a power source 28, such as an external pulsed high voltage source or a laser source. In some examples, the power source 28 is configured to selectively apply power to one or more emitters included in the shock wave generator 16, such that an operator of the catheter can selectively generate shock waves to treat different areas of a body lumen during a shock wave treatment.

The catheter 10 also includes a flexible shaft 12 that extends from the proximal end 22 to the distal end 14 of the catheter. The shaft 12 provides various internal conduits connecting elements of the distal end 14 with the proximal end 22 of the catheter. The shaft 12 includes a hollow tubular body that includes a lumen for receiving the guide wire 20. The hollow tubular body may include additional lumens extending through the shaft 12 or along an outer surface of the shaft 12. For example, one or more fluid lumens (e.g., a fluid inlet lumen and a fluid outlet lumen or a combined flush lumen) can be provided in the shaft 12 for carrying conductive fluid from the fluid port 26 into the enclosure 18, and one or more wire lumens can be provided for carrying conductive wires or optical fibers.

In operation, a physician advances the guide wire 20 from an entry site on a patient (e.g., an artery in the groin area of the leg) to the target region of a vessel (e.g., a region having an occlusion that needs to be broken up). The catheter 10 is then advanced over the guide wire 20 to the target region of the vessel. In some examples, the catheter 10 is a so-called "rapid exchange-type" ("Rx") catheter provided with an opening portion through which a guide wire 20 is guided (e.g., through a middle portion of a central tube in a longitudinal direction). In other examples, the catheter may be an "over-the-wire-type" ("OTW") catheter in which a guide wire lumen is formed throughout the overall length of the catheter, and a guide wire 20 is guided through the proximal end of a hub.

In one or more examples, the enclosure 18 sealed to the distal end 14 is a no-fold balloon having a low profile when deflated, such that the balloon does not need to be folded while the device is advanced through the vasculature. In other examples, the enclosure 18 may be membrane that is held in tension by a frame that can flex outwardly when pressurized with conductive fluid. During the positioning stage of treatment, a guide catheter or outer jacket may be used to aid the entry and maneuvering of the catheter 10 within the vasculature. The outer jacket can provide tubular linear support to the catheter shaft 12 and retain the shape of the enclosure 18 during pushing, crossing, and placement of the catheter 10. The in-situ location of the distal end 14 of the catheter 10 may be determined by x-ray imagining and/or fluoroscopy.

When treating a total occlusion, the guide wire 20 can be advanced at least partially into the lesion. The enclosure 18 is then pressurized with a conductive fluid (e.g., saline and/or saline mixed with an image contrast agent) that is introduced via the fluid port 26, allowing the conductive fluid to inflate the enclosure 18 so that the outer surface of the enclosure 18 contacts the target lesion. The enclosure 18 can be pressurized to IVL pressure, which can be between approximately one atmosphere and approximately six atmospheres. When depressurized, the diameter of the distal end 14 of the catheter 10 may be less than 1.5 mm. For instance, the overall diameter of the distal end 14 may be 1.0 mm 1.2 mm, 1.3, mm, or 1.4 mm, and increments and gradients of range therein. In one or more examples, the overall diameter of the distal end 14 may be less than 1.0 mm.

After inflating the enclosure 18, energy is supplied to one or more emitters of the shock wave generator 16 by an external power source 28 to generate shock waves. For electrohydraulic generation of acoustic shock waves, a voltage pulse may be delivered from the power source 28 to the emitter(s), resulting in an electrical discharge across electrode pairs of the emitter(s). This discharge creates one or more rapidly expanding vapor bubbles that generate the acoustic shock waves that propagate radially outward and through the enclosure 18 to modify calcified plaque within the blood vessels. In an alternative implementation, for laser generation of acoustic shock waves, the power source 28 generates a laser pulse that is transmitted into and absorbed by a fluid within the enclosure 18. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed.

Fluid can be continuously flowed into the enclosure 18 and evacuated from the enclosure via fluid lumens to clear bubbles and debris from the shock wave generator 16. The fluid flow rate may be controlled throughout treatment, but is generally constant and in the range of approximately one to five milliliters per minute (1-5 ml/min). In various examples, fluid may be flowed through the enclosure 18 using a syringe pump, a diaphragm pump, or an indeflator at a pressure between about two atmospheres (2 atm) and about six atmospheres (6 atm).

For treatment of occlusions in blood vessels with electrohydraulic shock waves, the voltage pulse applied by the power source 28 is typically in the range of about five hundred to about ten thousand volts (500 V-10,000 V), and in some examples may be no greater than four thousand volts (4,000 V). The repetition rate or frequency of the applied voltage pulses may be between about four hertz (4 Hz) and about one hundred hertz (100 Hz). The total number of pulses applied by the voltage source 28 may be, for example, sixty (60) pulses, eighty (80) pulses, one hundred twenty (120) pulses, three hundred (300) pulses, up to five hundred (500) pulses, or other increments of pulses within this range. The preferred voltage, repetition rate, and number of pulses may vary depending on, e.g., the size of the lesion, the extent of calcification, the size of the blood vessel, the attributes of the patient, the emitters being operated, or the stage of treatment. For instance, a physician may start with low energy shock waves and may increase the energy as needed during the procedure, or vice versa. The magnitude of the shock waves can be controlled by controlling the voltage, current, duration, and repetition rate of the pulsed voltage from the power source 28. More information about the physics of shock wave generation and their control can be found in U.S. Pat. Nos. 8,956,371; 8,728,091; 9,522,012; and 10,226,265, each of which is incorporated by reference.

In some examples, a physician may begin the procedure by generating one or more shock waves at a distal emitter of the shock wave generator 16 in order to cause the impactor to deliver mechanical forces to penetrate and clear occlusions distal to the distal end of the catheter. The physician may then generate one or more shock waves at one or more proximal emitters of the shock wave generator 16 to treat lesions surrounding the enclosure 18. However, a physician may operate the catheter 10 to generate shock waves at any desired emitters during various stages of a shock wave treatment (e.g., firing all emitters simultaneously, or by firing the emitters in any desired sequence). The progress of the procedure may be monitored by x-ray and/or fluoroscopy. As the lesion is broken up or loosened by the shock waves, the guide wire 20 and catheter 10 can be advanced farther into the lesion, and the shock wave treatment can be repeated until the total occlusion is cleared or until the diameter of the vessel permits the placement of a second treatment device having a larger profile. For example, the enlarged channel can receive a different catheter having a more conventional angioplasty balloon or differently oriented shock wave sources. Catheters of this type are described in U.S. Pat. No. 8,747,416 and U.S. Publication No. 2019/0150960, cited above. Once the lesion has been sufficiently treated, the catheter 10 and the guide wire 20 can be withdrawn from the patient.

Figure 2A:
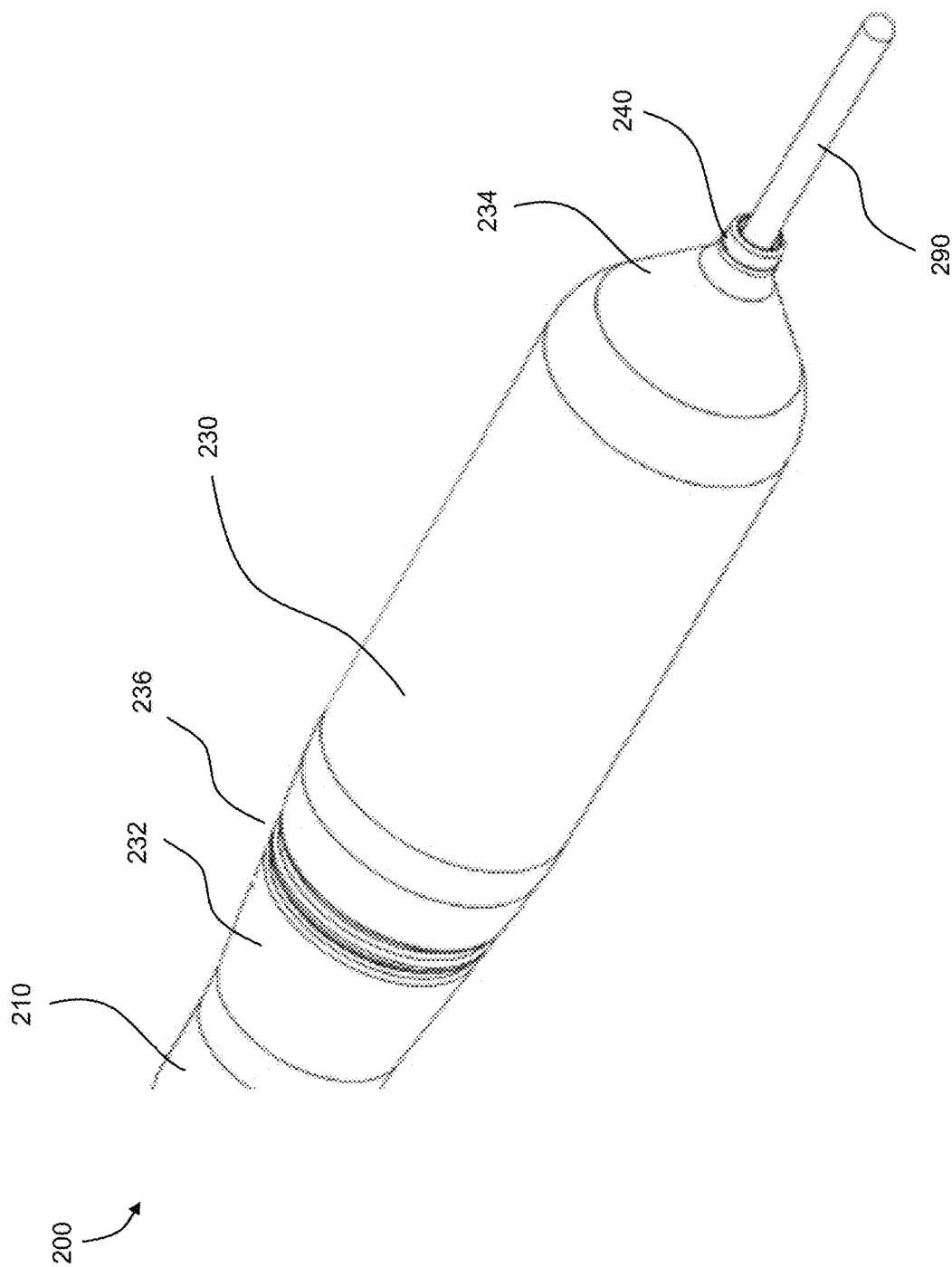
FIGS. 2A-2B illustrate the distal end of an exemplary catheter, according to one or more examples of the present disclosure.
Figure 2B:
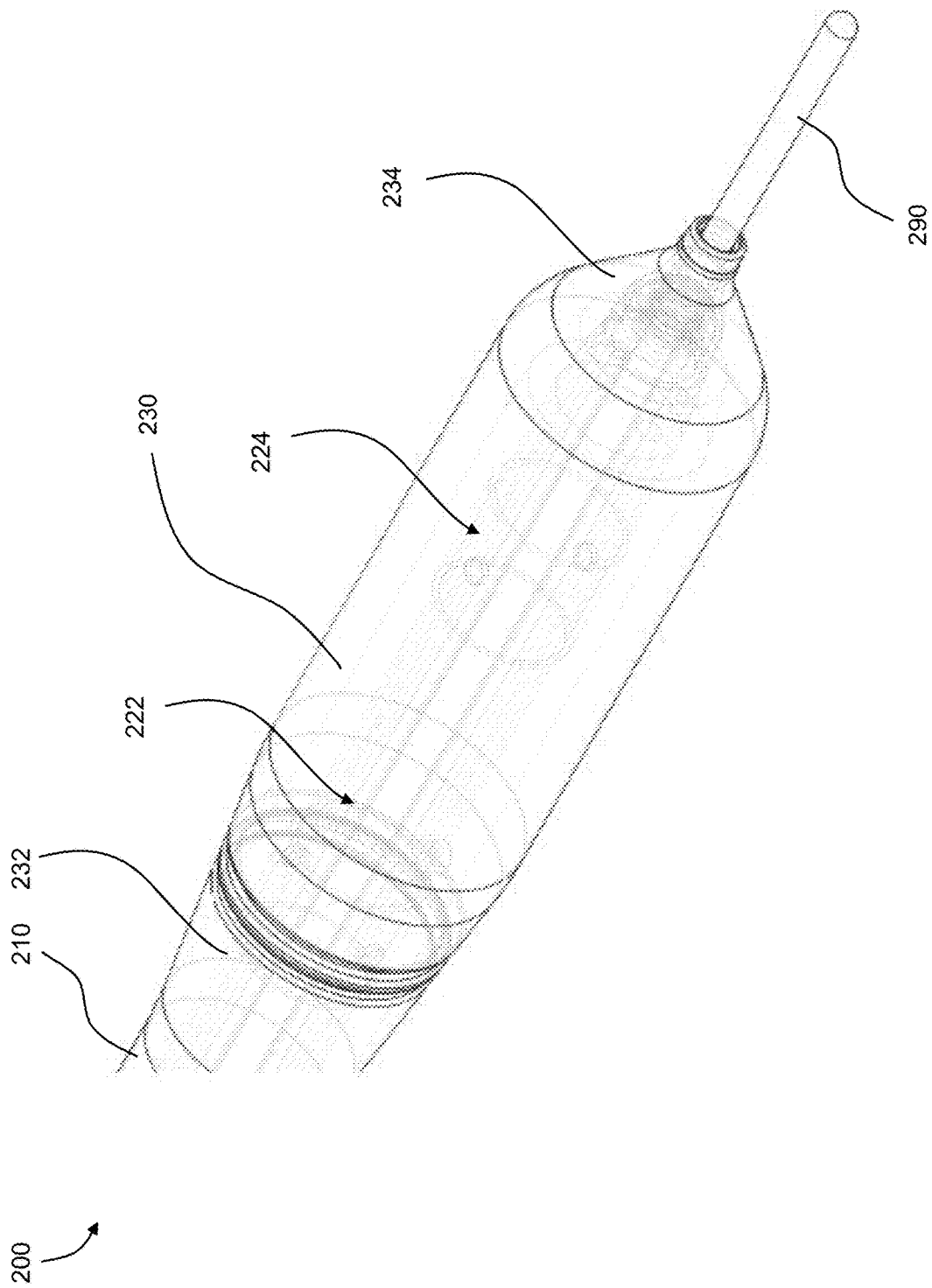

FIGS. 2A-2B illustrate the distal end of one exemplary catheter 200 of the present disclosure, which may be an example of the catheter 10 shown in FIG. 1 or any of the catheters described elsewhere in the disclosure. As seen in FIG. 2A, the catheter 200 includes a hollow tubular body 210 that extends axially along the length of the catheter. The hollow tubular body 210 may be formed from a rigid polymer or a semi-compliant polymer. The hollow tubular body 210 may include one or more lumens extending axially through the tubular body, such as lumens for carrying conductors (e.g., electrically conductive wires or optical fibers), fluid (e.g., a conductive fluid, such as saline), and/or a guide wire 290. The guide wire 290 may be used to facilitate insertion of the distal end of the catheter 200 into a body lumen and/or the advancement of the distal end to a position in the body lumen proximate to an occlusion.

In one or more examples, an enclosure 230 surrounds at least a portion of the hollow tubular body 210 near the distal end of the catheter 200. When the enclosure 230 is filled with a fluid, the enclosure forms an annular channel around a portion of the hollow tubular body 210. The enclosure 230 includes a proximal end 232 and a distal end 234, and the enclosure may be sealed to a portion of the catheter 200 at its distal and/or proximal ends. For instance, the proximal end 232 of the enclosure 230 may be sealed to a region of the hollow tubular body 210 (e.g., a proximal portion of the hollow tubular body). In some examples, the distal end 234 of the enclosure 230 is sealed to an impactor 240 of the catheter, such that a proximal portion of the impactor is inside the enclosure and a distal portion of the impactor is outside of the enclosure. However, in other examples the enclosure 230 may be sealed to a different region of the catheter 200. The enclosure 230 may include one or more features, such as a region with bellows 236, that allow the enclosure to extend and contract in length responsive to forward and backward movement of the impactor. The bellows 236 may be formed from a folded (e.g., accordion-shaped) region of the enclosure material that unfolds to extend the length of the enclosure. In some examples, the bellows 236 apply a spring-like restorative force to the impactor that causes the impactor and associated components to return to a proximal position after advancing in a distal direction.

In one or more examples, the enclosure 230 is an angioplasty balloon, such as an inflatable angioplasty balloon formed from a flexible polymer. In such examples, filling the enclosure 230 with fluid may cause the enclosure to inflate such that an inner surface of the enclosure is spaced apart from an outer surface of the hollow tubular body 210 to form an annular channel around the hollow tubular body. When the distal end of the catheter 200 is positioned in a body lumen, the enclosure 230 can be inflated with fluid such that the enclosure inflates and an outer surface of the enclosure contacts the walls of the body lumen (and/or a lesion proximate to walls of the body lumen). In some examples, the enclosure 230 is inflatable by a relatively lesser amount when filled with fluid, or may not inflate when filled with fluid. For instance, in one or more examples the enclosure 230 may be formed from a relatively more rigid material, such as a rigid or semi-compliant polymeric material.

The catheter further includes an impactor 240 mounted to a distal portion of the hollow tubular body 210. A proximal portion of the impactor 240 may be inside the enclosure 230, while a distal portion of the impactor is outside the enclosure. In one or more examples, the impactor 240 includes one or more conductive portions that serve as electrodes in one or more electrode pairs forming a distal emitter of the catheter 200. Accordingly, in some examples, at least a portion of the impactor 240 may serve as a portion of a distal emitter of the catheter 200. In such examples, the impactor 240 may be used to generate one or more shock waves inside a distal region of the enclosure 230 near the enclosure's distal end 234. When shock waves are generated near a proximal end of the impactor 240, the shock waves cause the impactor to advance in a distal (e.g., forward) direction relative to the catheter such that a distal portion of the impactor delivers a mechanical force to an occlusion. Accordingly, the shock waves generated at the conductive regions of the impactor 240 (e.g., the distal emitter) may serve to drive the movement of the impactor to treat occlusions proximate to the catheter's distal end. The shock waves generated at the conductive regions of the impactor 240 may also produce acoustic shock wave energy that propagates inside the enclosure 230 (e.g., to treats lesions in body lumens proximate to the outer surface of the enclosure). As the impactor moves in the distal direction, the impactor 240 may also cause the enclosure 230 to extend in length to accommodate the movement of the impactor 240. As mentioned above, a region of the enclosure 230 may include bellows 236 or some other feature(s) that allows the length of the enclosure to extend and contract in conjunction with the forward and backward (i.e., distal and proximal) movement of the impactor 240.

In some examples, and as shown in FIG. 2B, the catheter 200 may additionally include one or more proximal emitters 222, 224 for generating shock waves in more proximal regions of the enclosure 230 (e.g., regions in a central portion of the enclosure or regions near the proximal end 232 of the enclosure). The proximal emitters 222, 224 are disposed on the hollow tubular body 210 and surrounded by the enclosure 230 such that shock waves generated at the proximal emitters cause acoustic energy to propagate through the walls of the enclosure and into regions of the body lumen proximate to the outer surface of the enclosure. In the example shown in FIG. 2B, the catheter 200 includes a first proximal emitter 222 and a second proximal emitter 224. However, as explained below, a catheter 200 could include any number of proximal emitters.

Figure 3:
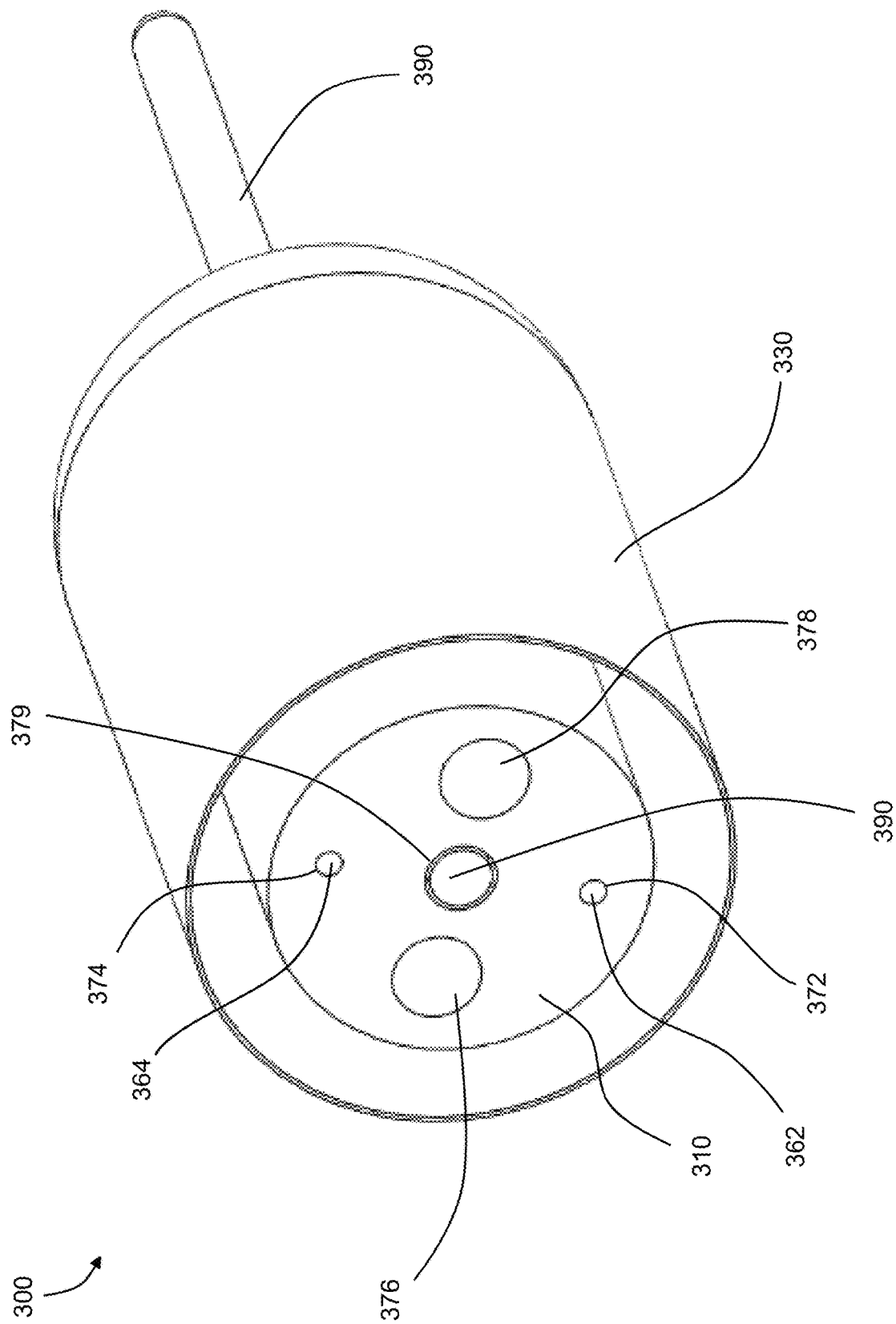
FIG. 3 illustrates a cross-sectional perspective view of the distal end of an exemplary catheter showing internal structures of the catheter, according to one or more examples of the present disclosure.

FIG. 3 illustrates a cross sectional perspective view of the distal end of an exemplary catheter 300 showing the internal structure of the hollow tubular body 310. The catheter 300 may be either of the catheters 10, 200 shown in FIGS. 1 and 2A-2B or any of the catheters described elsewhere in the disclosure, and may include similar components, such as a hollow tubular body 310 and an enclosure 330 surrounding at least a portion of the hollow tubular body. The view of FIG. 3 shows the enclosure 330 in an inflated state, such that the inner surface of the enclosure is not in contact with the outer surface of the hollow tubular body 310.

As described previously, the hollow tubular body 310 may include one or more lumens extending axially through the hollow tubular body. For instance, the hollow tubular body 310 may include one or more wire lumens for carrying wires (e.g., electrically conductive wires or optical fibers) between a power source and the shock wave emitters of the catheter 300. In one or more examples, the catheter includes a first wire lumen 372 for carrying a first wire 362 and a second wire lumen 374 for carrying a second wire 364. However, the hollow tubular body 310 may optionally include additional lumens for carrying additional wires. For instance, in some examples, the catheter includes a third wire lumen for carrying a third wire and/or a fourth wire lumen for carrying a fourth wire. In yet further examples, the wires of the catheter may extend along a surface the hollow tubular body 310 external to the hollow tubular body. For instance, one or more of the wires could be disposed in grooves that extend longitudinally along the outer surface of the hollow tubular body 310.

The hollow tubular body 310 may further include one or more fluid lumens for carrying fluid between a proximal end of the catheter (e.g., a fluid entry port in a proximal end handle, as shown in FIG. 1) and a distal end of the catheter (e.g., into the enclosure 330). For instance, the hollow tubular body may include a first fluid lumen 376 for carrying fluid toward the distal end of the catheter 300 and a second fluid lumen 378 for carrying fluid away from the distal end of the catheter.

As shown in FIG. 3, the wire lumens 372, 374 and/or fluid lumens 376, 378 extend axially through the hollow tubular body 310 and may be offset from a central longitudinal axis of the hollow tubular body. In some examples, the wire lumens 372, 374 and/or fluid lumens 376, 378 are positioned at predetermined locations with respect to the longitudinal axis of the hollow tubular body 310. For instance, a first wire lumen 372 may be positioned approximately 180 degrees about the central longitudinal axis of the catheter from a second wire lumen 374. Advantageously, this may position the first wire 362 and the second wire 362 in locations closer to the shock wave generating regions (i.e., the spark gaps) of the emitters disposed on the hollow tubular body 310 (for instance, in examples where the emitters are positioned or rotated to generate shock waves in opposite directions outward from the central longitudinal axis of the catheter 300). In one or more examples, a first fluid lumen 376 is positioned approximately 180 degrees about the longitudinal axis of the catheter from a second fluid lumen 378.

In one or more examples, the hollow tubular body 310 may further include a guide wire lumen 379. The guide wire lumen 379 may extend axially through the hollow tubular body 310 approximately along the central longitudinal axis of the hollow tubular body. The guide wire lumen 379 may be sized to receive a guide wire 390, such as a commercially available guide wire used in angioplasty procedures. Accordingly, the diameter of the guide wire lumen 379 may be approximately equal to the diameter of a guide wire plus an additional tolerance to allow the hollow tubular body 310 to slide easily along the guide wire 390 without resistance.

Figure 4:
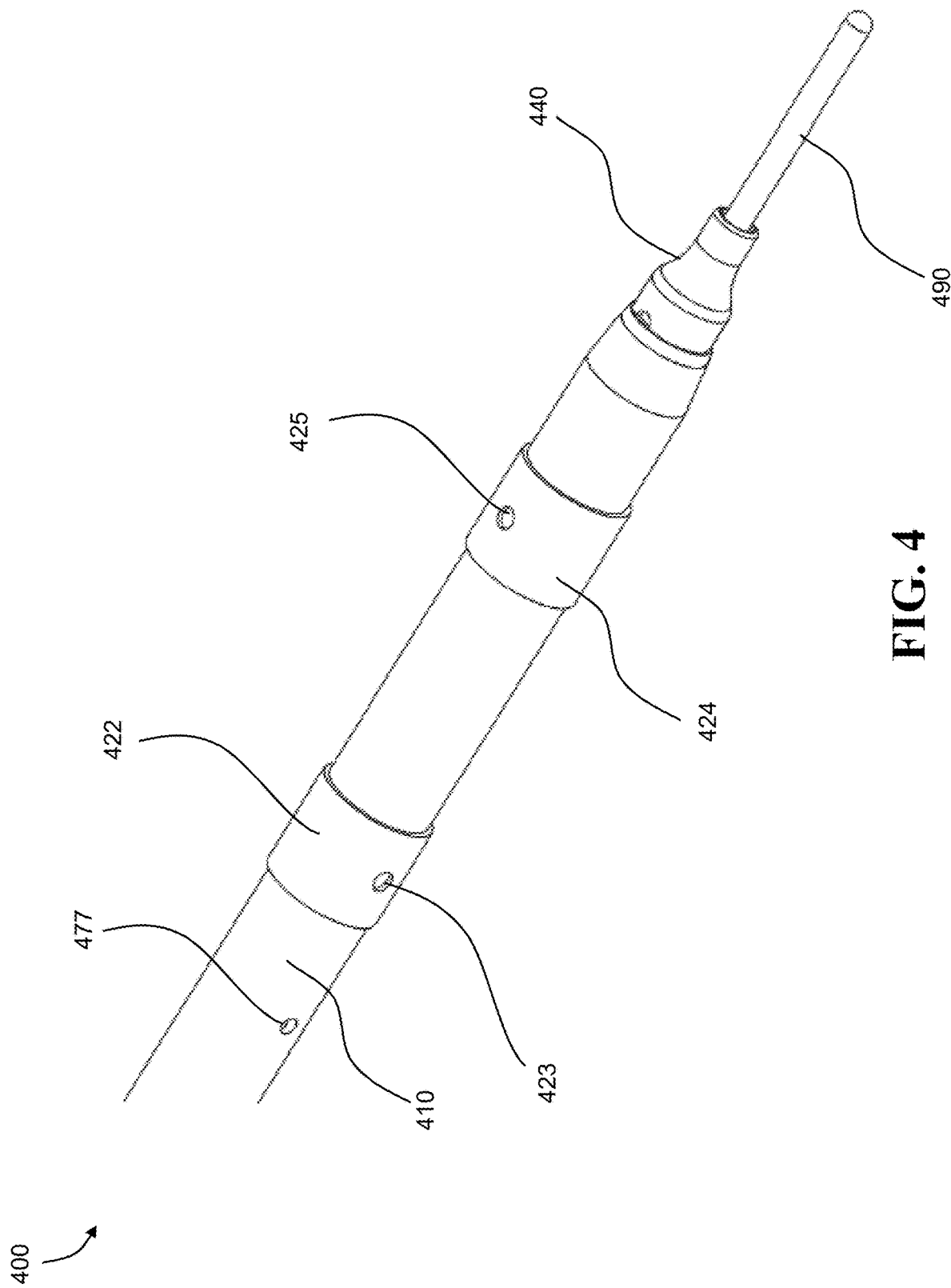
FIG. 4 illustrates a perspective view of the distal end of an exemplary catheter with the enclosure removed, according to one or more examples of the present disclosure.

FIG. 4 illustrates a view of the distal end of an exemplary catheter 400 with the enclosure removed. The catheter 400 may be any one of the catheters 10, 200, and 300 shown in FIGS. 1, 2A-2B, and 3 or any of the catheters described elsewhere in the disclosure, and may include similar components, such as a hollow tubular body 410, an impactor 440, and one or more proximal emitters 422, 424. The catheter 400 is shown with a guide wire 490 extending through a central guide wire lumen of the hollow tubular body 410. The hollow tubular body 410 additionally includes a fluid outlet 477 for flowing fluid through an enclosure (not shown) of the catheter 400.

As seen in FIG. 4, the catheter 400 includes a plurality of emitters, such as an impactor 440 that forms a portion of a distal emitter, a first proximal emitter 422, and a second proximal emitter 424. The proximal emitters 422, 424 are disposed on a region of the hollow tubular body 410 of the catheter 400 and may be mounted to the hollow tubular body by way of an adhesive. In some examples the proximal emitters 422, 424 are mounted to the hollow tubular body 410 by a mechanical fit (e.g., by sliding the emitters over the hollow tubular body and/or mechanically compressing the emitters onto the hollow tubular body) or by forming a portion of the hollow tubular body around the emitters (e.g., by shrinking the material of the hollow tubular body around the emitters). In some examples, the proximal emitters 422, 424 are inset into the material of the hollow tubular body 410. However, in other examples the proximal emitters 422, 424 rest on an outer surface of the hollow tubular body 410 and/or project outwardly from the hollow tubular body.

The proximal emitters 422, 424 may be formed of an electrically conductive material, such that a current can flow across the emitters and between the emitters and other conductive elements (e.g., electrically conductive wires) to generate one or more shock waves. In some examples, the proximal emitters 422, 424 are formed from a metal, such as stainless steel, nickel, titanium, tungsten, platinum, palladium, molybdenum, or alloys thereof. In some examples, the proximal emitters 422, 424 are configured as conductive metal sheaths or bands and are configured to encircle around at least a portion of the circumference of the hollow tubular body 410. In some examples, the conductive metal sheaths are continuous (i.e., cylindrically shaped, such that the emitters encircle the entire circumference of the hollow tubular body 410). However, in other examples the conductive metal sheaths are discontinuous (i.e., encircling only a portion of the circumference of the hollow tubular body 410).

In some examples, each of the proximal emitters 422, 424 includes a conductive portion that forms an electrode of at least one electrode pair. The conductive portion may be positioned adjacent to a conductor, such as the distal tip of an electrically conductive wire, such that, when a voltage pulse is applied to the conductor, current can flow between the conductor and the conductive portion to generate shock waves at one or more of the proximal emitters 422, 424. In some examples, the conductive portion includes an edge of the emitter. For example, the conductive portion could include an inner edge formed by an aperture that extends through the emitter (e.g., the first aperture 423 through the first proximal emitter 422, and the second aperture 425 through the second proximal emitter 424).

While the catheter 400 of FIG. 4 is shown with two proximal emitters 422, 424, a catheter could incorporate a greater or lesser number of proximal emitters. For instance, the catheter 400 could include zero (0) proximal emitters, one (1) proximal emitter, two (2) proximal emitters, three (3) proximal emitters, four (4) proximal emitters, five (5) proximal emitters, six (6) proximal emitters, seven (7) proximal emitters, or eight (8) proximal emitters. In some examples, the catheter 400 includes at least two (2) proximal emitters, at least three (3) proximal emitters, at least four (4) proximal emitters, at least five (5) proximal emitters, at least six (6) proximal emitters, at least seven (7) proximal emitters, or at least eight (8) proximal emitters. While some additional exemplary embodiments of the disclosure may not show similar proximal emitters, it should be understood that any of the catheter described herein may include any number of proximal emitters (or no proximal emitters).

In one or more examples, the proximal emitters may be arranged to promote more effective shock wave treatments. For instance, the proximal emitters may be oriented (e.g., rotationally oriented or "clocked") with respect to the central longitudinal axis of the catheter 400 such that shock waves are emitted in different radial directions around the circumference of the catheter. For instance, in some examples, the rotational orientation of a first proximal emitter 422 is 180 degrees apart with respect to the rotational orientation of a second proximal emitter 424. However, in other examples, the rotational orientation of a first proximal emitter 422 is thirty (30) degrees, forty-five (45) degrees, sixty (60) degrees, ninety (90) degrees, or one hundred twenty (120) degrees apart with respect to the rotational orientation of a second proximal emitter 424. In some examples, each of a plurality of proximal emitters is rotationally oriented such that the plurality the proximal emitters are oriented in equally spaced direction around the circumference of the catheter, e.g., so as to promote shock wave generation evenly around the circumference of the catheter. In some examples, the distance between adjacent proximal emitters is selected to promote constructive interference between shock waves generated at adjacent proximal emitters. For instance, the distance between the first proximal emitter 422 and the second proximal emitter 424 could be between about one millimeter (1 mm) and about four millimeters (4 mm).

In some examples, the proximal emitters 422, 424 are operable independently from a distal emitter (e.g., a distal emitter formed at least partially from the impactor 440) of the catheter 400. For instance, a physician operating the catheter may choose to selectively activate either a distal emitter or one or more proximal emitters 422, 424 in order to, e.g., selectively treat either an occlusion distal to the catheter near the impactor 440 or a more proximal region of the body lumen surrounding the enclosure 430 and proximal emitters. In a particular example, a physician may first operate a distal emitter to penetrate and rupture an occlusion near the catheter's distal tip, before operating the proximal emitters 422, 424 (optionally after advancing the catheter further in the body lumen) to treat occluded regions and lesions positioned radially around the distal end of the catheter 400.

Figure 5A:
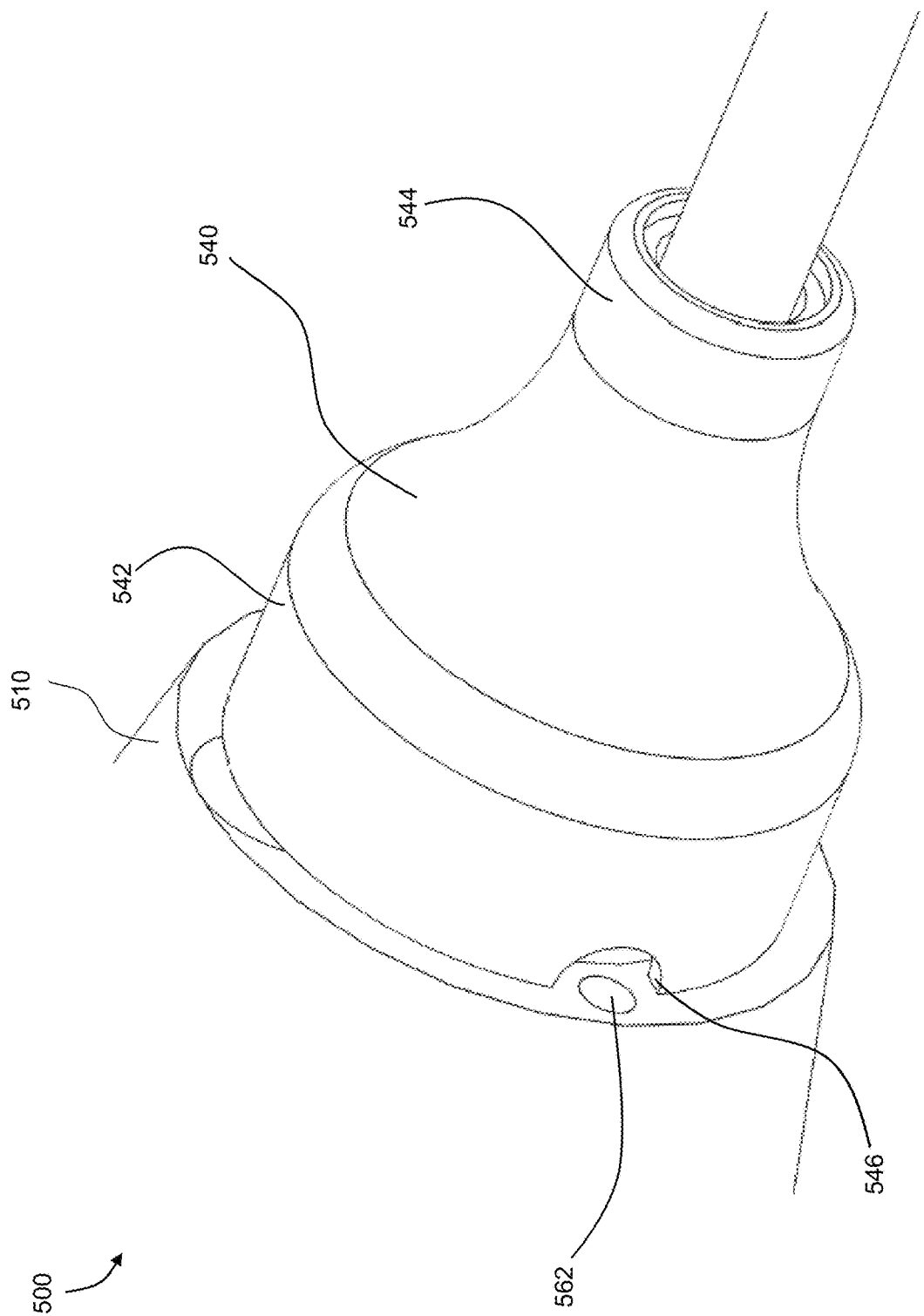
FIGS. 5A-5B illustrate close-up perspective views of the distal end of an exemplary catheter, according to one or more examples of the present disclosure.
Figure 5B:
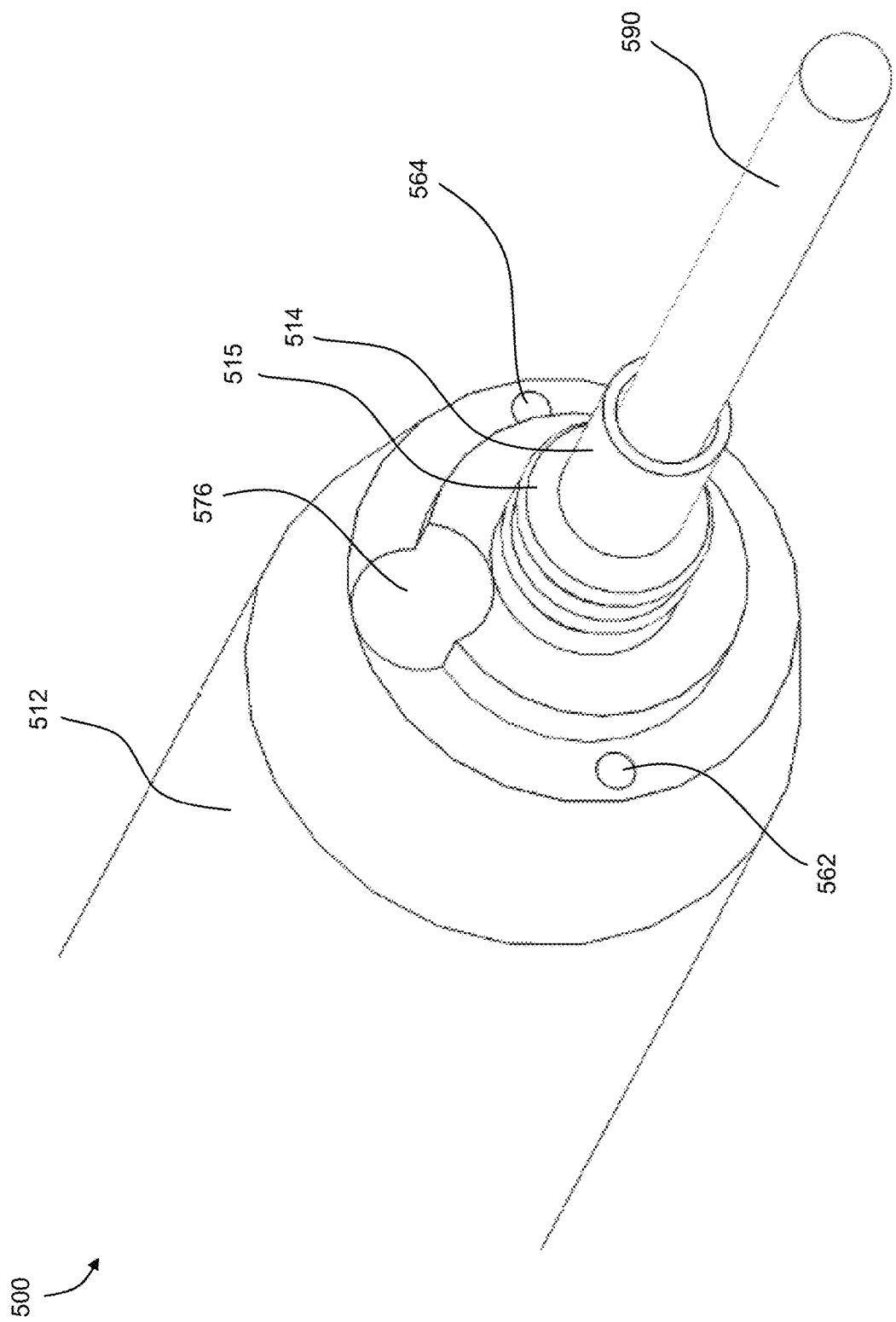

The impactor 440 of the catheter 400 is mounted on a distal portion of the hollow tubular body 410, for instance, by way of an adhesive or a mechanical fit. In some examples, the impactor 440 is mounted on the hollow tubular body 410 by interlocking a portion of the impactor with the hollow tubular body, such as by laser-cutting or micro-molding. In yet further examples, the impactor 440 may be formed integrally from a portion of the hollow tubular body 410, such as formed integrally with a distal portion of the tubular body (e.g., distal portion 514). The impactor 440 is positioned such that shock waves generated by a distal emitter impinge on the impactor to cause the impactor to advance in a distal direction relative to the hollow tubular body 410. FIG. 5A illustrates a close-up perspective view of the distal end of an exemplary catheter 500 showing an exemplary impactor 540 of the catheter. FIG. 5B illustrates an additional close-up perspective view of the catheter 500 with the impactor 540 removed to show bellows 515 formed in the hollow tubular body 510 that permit the advancement of the distal portion 514 of the hollow tubular body and the impactor 540 relative to a proximal portion 512 of the hollow tubular body. The catheter 500 shown in FIGS. 5A-5B may be any one of the catheters 10, 200, 300, and 400 described previously with respect to FIGS. 1-4 or any of the catheters described elsewhere in the disclosure, and may include similar components, such as a hollow tubular body 510 with lumens configured to receive, e.g., a guide wire 590 and one or more conductors (e.g. a first conductor 562 and a second conductor 564), and at least one fluid lumen 576.

A proximal end 542 of the impactor 540 may be positioned proximate to a proximal portion 512 of the hollow tubular body 510, while a distal end 544 of the impactor is oriented away from the hollow tubular body and is used to impart mechanical forces on occlusions distal to the hollow tubular body. The distal end 544 of the impactor 540 may have a relatively smaller surface area than the proximal end 542, such that, when a shock wave impinges on a proximal end of the impactor and causes the impactor to advance in a distal direction, the mechanical force delivered to the occlusion by the distal end of the impactor is distributed over a smaller surface area and therefore applies a greater amount of pressure to the occlusion. For instance, in some examples, the impactor 540 tapers from a proximal end 542 to a distal end 544. In some examples, the distal end 544 of the impactor includes features for increasing the force applied to an occlusion when the impactor is advanced into an occlusion. For instance, the distal end 544 of the impactor 540 may include a sharpened edge, one or more protrusions, one or more teeth, or one or more other features designed to increase the effectiveness of the impactor at breaking up occlusions in body lumens.

In one or more examples, the impactor 540 is mounted to a distal portion 514 of the hollow tubular body 510. For instance, the hollow tubular body 510 may include a proximal portion 512 and a distal portion 514 extending distally from the proximal portion with respect to the orientation of the catheter 500. The distal portion 514 may have a reduced diameter relative to the proximal portion 512. In one or more examples, the distal portion 514 of the hollow tubular body 510 is configured to move in conjunction with the impactor 540 during a shock wave treatment. For instance, the distal portion 514 may be configured to move distally relative to the proximal portion 512 (i.e., away from the proximal portion) when the impactor 540 is advanced in a distal direction responsive to the generation of a shock wave, and further to move proximally relative to the proximal portion (i.e., closer to the proximal portion) when the impactor returns in a proximal direction following the termination of a shock wave. In some examples, the distal portion 514 and/or proximal portion 512 includes features (e.g., bellows 515) that allow the impactor and the distal portion to move relative to the proximal portion.

As previously mentioned, a portion of the impactor 540 may serve as at least a portion of a distal emitter of the catheter 500 and may be used to generate shock waves near the distal end of the catheter. Accordingly, the impactor 540 may be formed at least partially from a conductive material similarly to the proximal emitters 422, 424 shown in FIG. 4 and described above. In some examples, the impactor 540 may be formed from a single material, such as a conductive material. In some examples, the conductive material is a metal, such as stainless steel, nickel, titanium, tungsten, platinum, palladium, molybdenum, or alloys thereof. In a more particular example, the impactor 540 may include a conductive metal sheath that encircles at least a portion of the circumference of the distal portion 514 of the hollow tubular body 510. However, in one or more examples, at least a portion of the impactor 540 is not formed from a conductive material. For instance, at least a portion of the conductor may be formed from a rigid or heat-resistant polymer, e.g., Teflon, parylene, PEEK (Polyether Ether Ketone), or ULTEM (Polyetherimide: PEI). In some examples, the impactor 540 may be formed from a plurality of materials that have been integrated to form the impactor. For instance, a first portion of the impactor 540 (e.g., a proximal portion near the proximal end 544) may be formed from a conductive material, while a second portion of the impactor (e.g., a distal portion near the distal end 542) may be formed from a nonconductive material, such as a polymer. In some examples the distal portion of the impactor 540 is formed from a rigid material, such as a metal, a ceramic, or a rigid polymer. In one or examples, the impactor 540 may be formed entirely from a non-conductive material. In such examples, a distal emitter may be separate from the impactor and disposed near a proximal end 542 of the impactor 540 such that shock waves generated at the distal emitter originate behind (i.e., proximal to) the impactor. For instance, a distal emitter could be included on a proximal portion 512 of the hollow tubular body 510, optionally with the emitter formed at least partially from a distal tip of one or more conductors 562, 564 extending through the hollow tubular body.

In one or more examples, the impactor 540 includes one or more conductive portions (e.g. conductive portion 546) that form a portion of the distal emitter. For instance, the one or more conductive portions may function as an electrode of an electrode pair of a distal emitter. In one or more examples, the proximal end 542 of the impactor includes the conductive portions. For instance, the conductive portions may be formed on a proximal edge of the impactor. In some examples, and as shown in FIG. 5A, the conductive portions include arcuate cut-outs in a proximal edge of the impactor. For instance, a first conductive portion 546 of the impactor may include a first cut-out in a proximal edge of the impactor, and a second conductive portion (not shown) of the impactor may include a second cut-out in the proximal edge of the impactor. When the impactor 540 is mounted on the hollow tubular body 510, the conductive portions of the impactor are positioned in close proximity to (e.g., adjacent to) the exposed distal tips of a pair of conductors (e.g., the first conductor 562).

Figure 6:
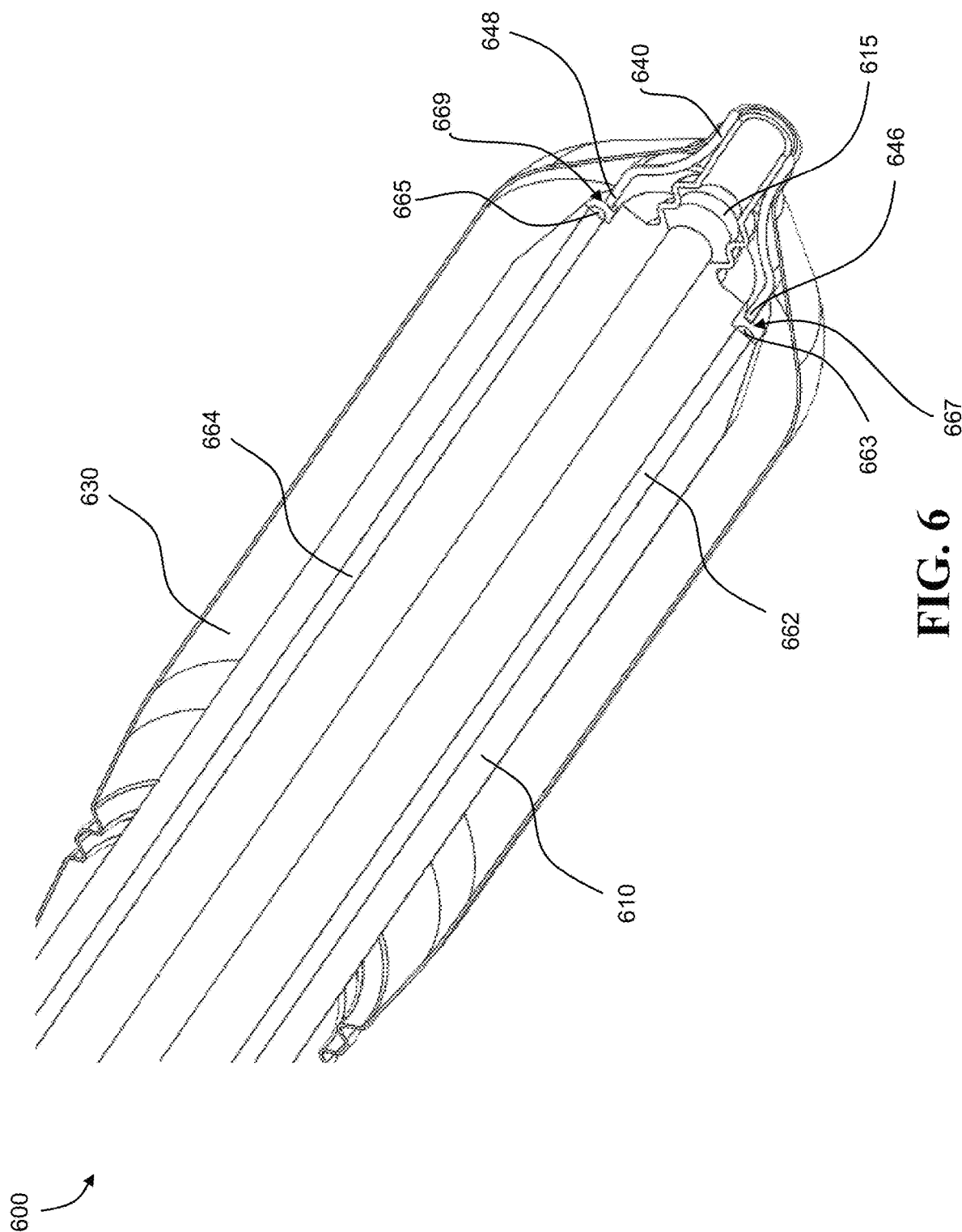
FIG. 6 illustrates a cross sectional perspective view of the distal end of an exemplary catheter showing the relationship between a pair of conductors and an impactor of the catheter, according to one or more examples of the present disclosure.

FIG. 6 illustrates a cross sectional perspective view of the distal end of an exemplary catheter 600 to show the relationship between the pair of conductors 662, 664 and the impactor 640. The catheter 600 may be any one of the catheters 10, 200, 300, 400, and 500 described previously with respect to FIGS. 1-5B or any of the catheters described elsewhere in the disclosure, and may include similar components, such as an impactor 640, a hollow tubular body 610 including an extending feature 615 to permit distal and proximal movement of the impactor, an enclosure 630, and a pair of conductors 662, 664 extending within lumens of the hollow tubular body. In one or more examples, the pair of conductors 662, 664 are electrically conductive wires (e.g., insulated copper or molybdenum wires wires). However, in other examples the pair of conductors 662, 664 include optical fibers. The proximal ends of the pair of conductors 662, 664 may be connected to a power source, such as a high voltage pulse generator or a laser power source (e.g., the power source 28 shown in FIG. 1). The exposed distal tips 663, 665 of the pairs of conductors 662, 664 are adjacent to the conductive portions 646, 648 of the impactor 640, such that, when a voltage is applied by the power source, current can flow between the distal tips of the pair of conductors and the conductive portions to generate shock waves. For instance, in some examples a first conductive portion 646 of the impactor 640 is adjacent to the distal tip 663 of a first wire 662, and a second conductive portion 648 is adjacent to the distal tip 665 of a second wire 664.

For instance, the pair of conductors may include a first insulated wire 662 having an exposed distal tip 663 and a second insulated wire 664 having an exposed distal tip 665. The distal tips 663, 665 of the pair of conductors 662, 664 may be spaced apart from the conductive portions 646, 648 of the impactor 640 by respective spark gaps 667, 669. For instance, the distal tip 663 of the first wire 662 may be spaced apart from the first conductive portion 663 by a first spark gap 667, and the distal tip 665 of the second wire 664 may be spaced apart from the second conductive portion 648 by a second spark gap 669. The spacing between the distal tips 663, 665 and the pair of conductors 662, 664 (i.e., the length of the spark gap) may be at least three thousandths of an inch (0.003") or at least five thousandths of an inch (0.005"). In some examples, the spacing between the distal tips 663, 665 and the pair of conductors 662, 664 is no greater than one hundredth of an inch (0.01") or no greater than eight thousandths of an inch (0.008"). In some examples, the spacing between the distal tips 663, 665 and the pair of conductors 662, 664 is between five thousandths of an inch (0.005") and eight thousandths of an inch (0.008"). Accordingly, in some examples, the distal tips 663, 665 of the wires 662, 664 may form a first electrode of a respective electrode pair, and a second electrode of each respective electrode pair may be formed by a conductive portion 646, 648 of the impactor 640.

In one or more examples, when a voltage pulse is applied across the first insulated wire 662 and the second insulated wire 664, a current is configured to flow from the exposed distal tip 663 of the first insulated wire 662 to the first conductive portion 646 of the impactor 640 across the first spark gap 667 to generate a first shock wave. In such examples, the current is further configured to flow from the second conductive portion 648 of the impactor 640 to the exposed distal tip 665 of the second insulated wire 664 across the second spark gap 669 to generate a second shock wave. Accordingly, applying a voltage pulse across the first insulated wire 662 and the second insulated wire 664 may cause the generation of at least two shock waves at spark gaps 667, 669 near the impactor 640.

As described previously and shown in FIG. 3, a catheter may further include one or more proximal emitters. Accordingly, the catheter 600 of FIG. 6 may additionally include one or more proximal emitters (not shown). In such examples, the proximal emitters may be operable to generate shock waves independently from a distal emitter of the catheter 600 (e.g., a distal emitter formed at least partially by the impactor 640). To enable the independent operation of the proximal emitter(s) and the distal emitter, in some examples, a second pair of conductors (e.g., a second pair of electrically conductive insulated wires or optical fibers) is provided. In some examples, the second pair of conductors may include a third insulated wire having an exposed distal tip adjacent to a conductive portion of a proximal emitter and a fourth insulated wire having an exposed distal tip adjacent to a further conductive portion of a proximal emitter. The distal tips of the second pair of conductors may be spaced apart from the conductive portions of the proximal emitters by respective spark gaps. Accordingly, in some examples, the distal tips of the third and fourth insulated wires may form a first electrode of a respective electrode pair, and a second electrode of each respective electrode pair may be formed by a conductive portion of a proximal emitter. When power is supplied by the power source across the second pair of conductors, current can flow between the distal tips of the second pair of conductors and the proximal emitters to generate shock waves at the proximal emitters. Thus, a physician may selectively generate shock waves at either one or more of the proximal emitters or at a distal emitter by selectively applying power across either the first pair of conductors or a second pair of conductors, and the voltage source may be configured for selectively applying power to generate shock waves at either the proximal emitter(s) or the distal emitter. Accordingly, a physician may choose to treat occlusions distal to the catheter by activating the distal emitter to advance the impactor into an occlusion and/or regions of the body lumen surrounding the enclosure and more proximate to the proximal emitter(s). In some examples, the shock waves generated at the proximal emitters do not cause the impactor to advance in the distal direction.

Figure 7:
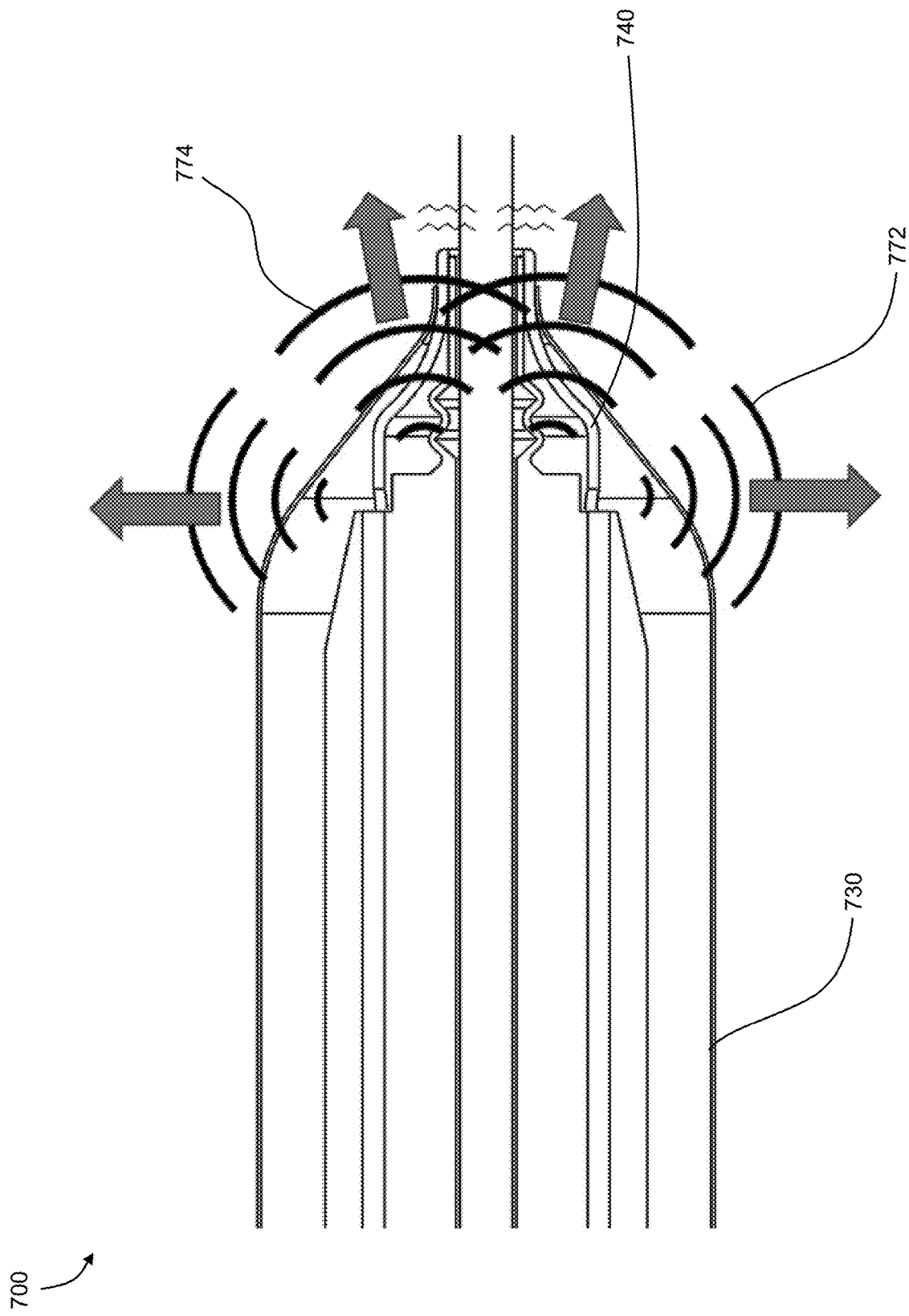
FIG. 7 illustrates an exemplary diagram showing the propagation of shock waves generated at a distal emitter of a catheter, according to one or more examples of the present disclosure.

Shock waves generated at the distal emitter and/or the proximal emitter(s) may propagate radially outward inside the enclosure 630. FIG. 7 illustrates an exemplary diagram of the propagation of shock waves generated at a distal emitter of a catheter 700, which may be any of the catheters 10, 200, 300, 400, 500, or 600 and shown in FIGS. 1-6 or any of the catheters described elsewhere in the disclosure. As seen in FIG. 7, at first radial portion 772 of the shock wave propagates in a radial direction relative to the longitudinal axis of the catheter 700, while a second axial portion 774 of the shock wave propagates axially relative to the longitudinal axis of the catheter in a distal direction. The radial portion 772 of the shock wave may propagate through an enclosure 730 of the catheter 700 and into calcified regions of a body lumen contacting the outer surface of the enclosure. The axial portion 774 of the shock wave may impinge on the impactor 740 to impart a mechanical force on the proximal end of the impactor that causes the impactor to advance in a distal direction and into an occlusion to deliver a mechanical force directly to the occlusion. Generating repeated shock waves may cause the impactor 740 to oscillate forward and backward to repeatedly deliver mechanical forces to the occlusion until the occlusion has been penetrated or ruptured and flow has been restored to the body lumen. In other embodiments, the distal region of the catheter 700 is configured such that the movement of the impactor 740 also has a lateral component (i.e., in a direction normal to the proximal-distal direction). For example, electrodes of the distal emitter (or distal ends of optical fibers for laser-generated shock waves) may be positioned such that mechanical force on the proximal end of the impactor favor one circumferential side. In such examples, the shock waves generated at one or more of the distal emitters may impinge on a particular circumferential side of the impactor 740 to cause movement of the impactor that includes a lateral component in the same circumferential direction.

Figure 8A:
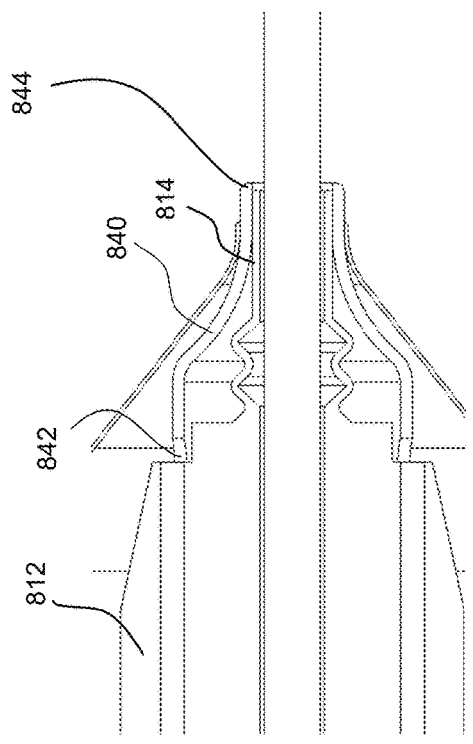
FIGS. 8A-8C illustrate cross-sectional views of the distal end of an exemplary catheter showing the movement of an impactor of the catheter, according to one or more examples of the present disclosure.
Figure 8B:
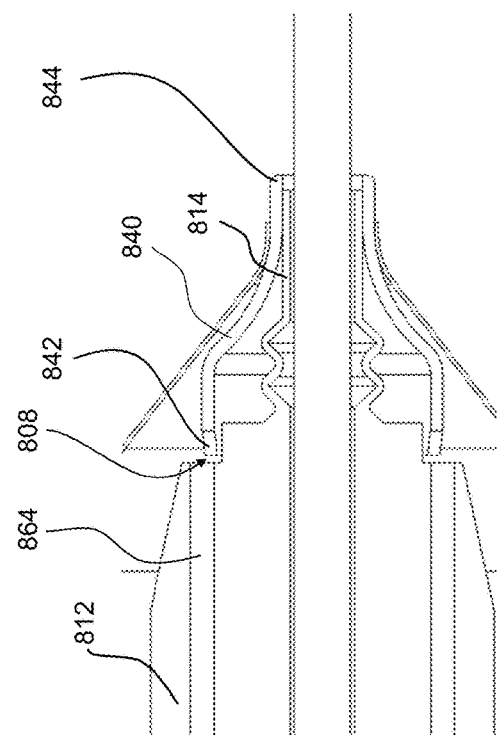
Figure 8C:
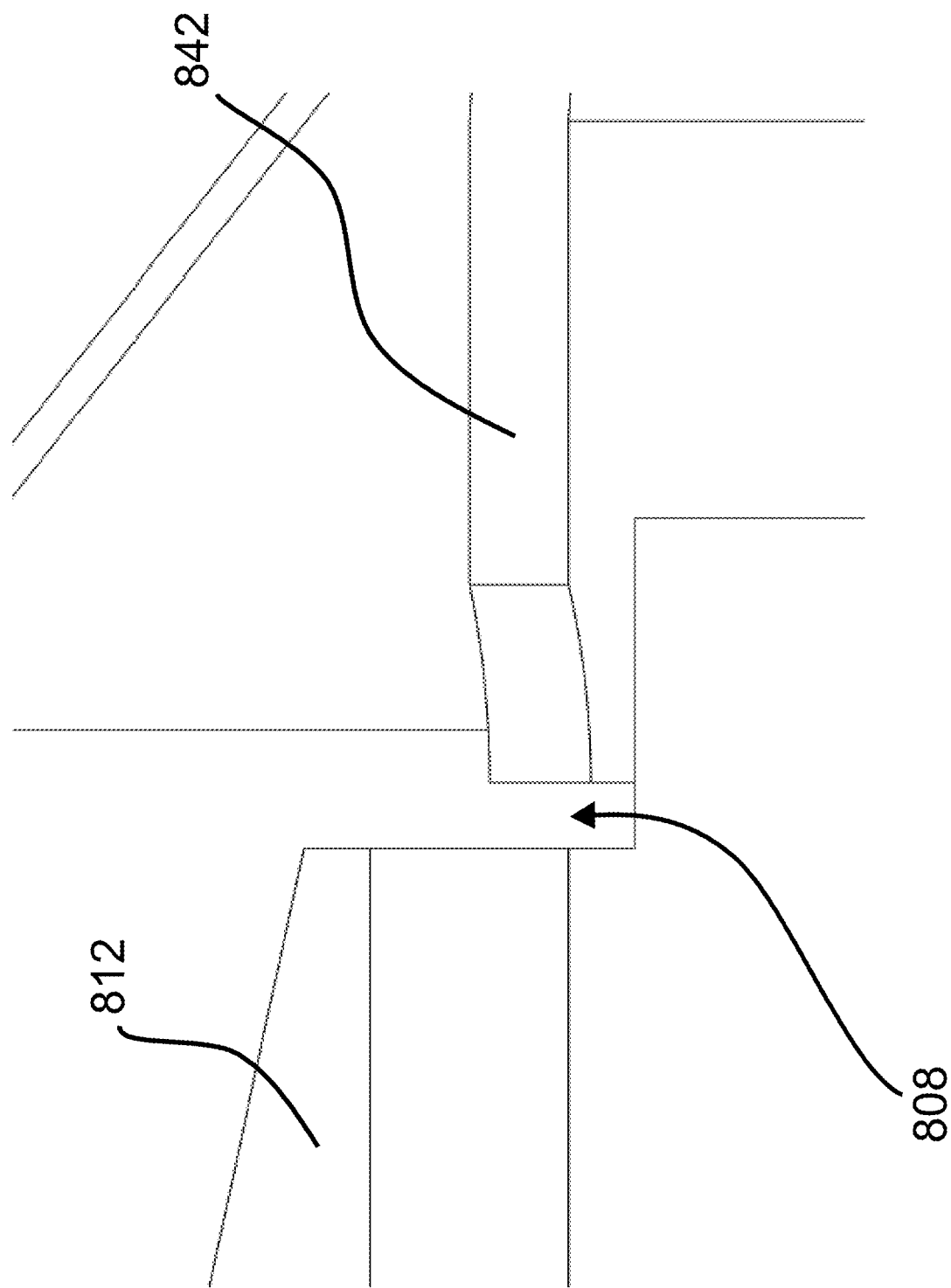

FIGS. 8A-8C illustrate cross sectional views of the distal end of an exemplary catheter 800 showing the movement of an impactor 840 of the catheter responsive to the generation of shock waves. The catheter 800 may be any one of the catheters 10, 200, 300, 400, 500, 600, and 700 illustrated in FIGS. 1-7 and described above or any of the catheters described elsewhere in the disclosure. FIG. 8A illustrates the catheter 800 in a first position prior to the generation of a shock wave, wherein a proximal end 842 of the impactor 840 is adjacent to (e.g., touching) a proximal portion 812 of the hollow tubular body 810. In some examples, in the first position, a small gap exists between the proximal end 842 of the impactor 840 and the proximal portion 812 of the catheter body. However, in other examples, and as shown in FIG. 8A, in the first position, the proximal end 842 of the impactor 840 is contacting the proximal portion 812 of the hollow tubular body. FIG. 8B illustrates the catheter 800 in a second position following the generation of a shock wave, wherein the impactor 840 has advanced in a distal direction such that there is a gap 808 between the proximal end 842 of the impactor 840 and the proximal portion 812 of the hollow tubular body and the distal end of the conductor 864. FIG. 8C illustrates a close up view of the distal end of the catheter 800 to show the gap 808 that forms between the proximal end 842 of the impactor 840 and the proximal portion 812 of the hollow tubular body when the catheter is in the second position (i.e., after the impactor has advanced in the distal direction). Following the generation of a shock wave (and prior to the generation of a second shock wave) the impactor 840 may return to the first position. In some examples, the impactor 840 may be configured to advance a relatively small distance responsive to the generation of shock waves, such as between about 50 micrometers (50 μm) and about 600 micrometers (600 μm). In some examples, the impactor is configured to advance less than about half a millimeter (0.5 mm) with respect to the proximal portion of the hollow tubular body 810. However, in other examples the impactor 840 may be configured to advance a relatively greater or lesser amount with respect to the proximal portion of the hollow tubular body 810, such as about a tenth of a millimeter (0.1 mm), about a quarter of a millimeter (0.25 mm), about a half of a millimeter (0.5 mm), about three quarters of a millimeter (0.75 mm), or about one millimeter (1 mm). In other examples, the impactor 840 may advance greater than one half millimeter (0.5 mm), or less than a quarter of a millimeter (0.25 mm).

In one or more embodiments, the distal movement of the impactor 840 is tuned by controlling the sonic output of the distal emitter. For example, the movement may be tunable to be between five hundredths of a millimeter (0.05 mm) and one millimeter (1 mm). The sonic output of the distal emitter may be controlled by adjusting the power applied to the emitter (e.g., by adjusting the voltage applied across electrodes).

As mentioned previously, the impactor 840 may be mounted on a distal portion 814 of the hollow tubular body and the distal portion 814 of the hollow tubular body moves in conjunction with the impactor such that, when the impactor advances in the distal direction, the distal portion of the hollow tubular body advances in conjunction with the impactor following the generation of a shock wave. The proximal portion 812 of the hollow tubular body may be configured to remain substantially stationary during the shock wave treatment, such that both the impactor 840 and the distal portion 814 advance in the distal direction relative to the proximal portion of the hollow tubular body. After the shock wave terminates, the impactor 840 and distal portion 814 may then return to a more proximal position nearer to (or contacting) the proximal portion 812.

To permit the advancement of the distal portion 814 of the hollow tubular body and the impactor 840 relative to the proximal portion 812 of the hollow tubular body, the catheter 800 may include one or more features that allow for the movement of the distal portion and the impactor relative to the proximal portion. After the distal advancement of the distal portion 814 and impactor 840, the features may also serve to force the distal portion and impactor in a proximal direction, e.g., by exerting a spring-like force to return the distal portion and impactor to a more proximal position closer to the proximal portion 812 of the hollow tubular body. Advantageously, these features allow for the distal and proximal movement of the impactor relative to the proximal portion of the hollow tubular body without damaging the material of the hollow tubular body or enclosure 830 of the catheter 800. In other words, such features of the catheter 800 allow for the oscillation motion of the impactor 840 along the longitudinal axis of the catheter 800 without tearing, ripping, or detachment of the enclosure 830 relative to the proximal portion of the hollow tubular body. As an additional advantage, the features may apply a proximally-directed force to the impactor to return the impactor 840 and distal portion 814 to a proximal position after advancement in the distal direction, such that the impactor may be advanced forward repeatedly during a shock wave treatment to apply repeated forces to an occlusion.

Figure 9A:
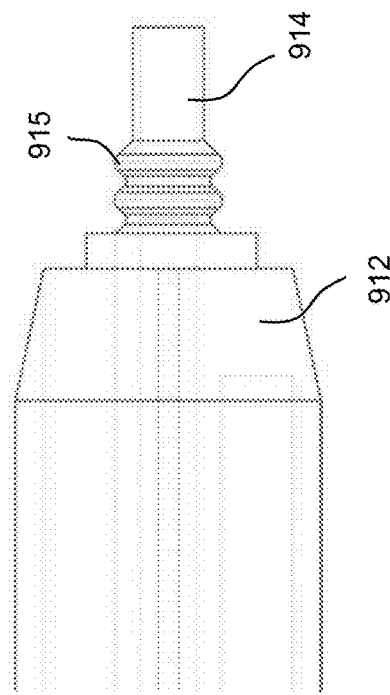
FIGS. 9A-9C illustrate various features of an exemplary catheter that permit the movement of an impactor relative to a proximal portion of the body of a catheter, according to one or more examples of the present disclosure.
Figure 9C:
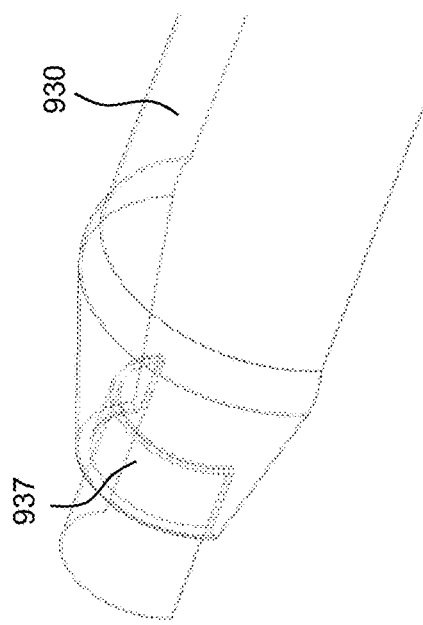
Figure 9B:
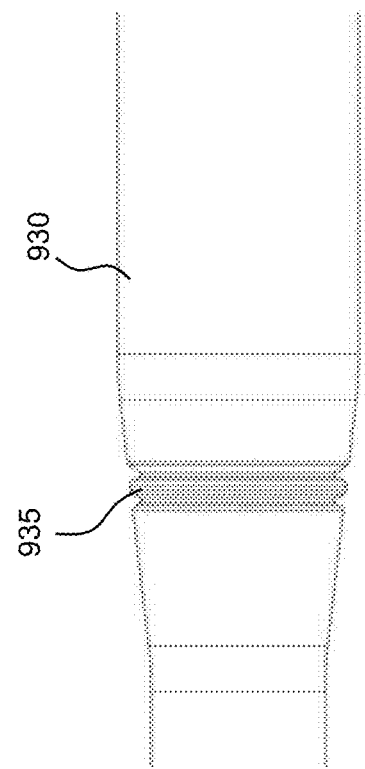

FIGS. 9A-9C illustrate various exemplary features that can be included in a catheter, such as any of the catheters described herein, to permit the forward and backward (i.e., distal and proximal) movement of an impactor and a distal portion of the catheter relative to a proximal portion of the catheter. For instance, FIG. 9A illustrates an example of distal bellows 915 that can be included in a distal portion 914 of a hollow tubular body of a catheter. The distal bellows 915 may be configured to extend to increase a length of the distal portion 914 of the hollow tubular body of the catheter when the impactor 940 advances in the distal direction responsive to the generation of a shock wave. The distal bellows 915 may be formed integrally with the distal portion 914, or may be formed from a second material adhered to the distal portion. The shape and/or material of the bellows (e.g., an accordion shape including one or more folds or material, or an elastic property of the material) may create a spring-like force for restoring the shape of the distal bellows and returning the distal portion 914 to its proximal position (e.g., the first position shown in FIG. 8A). Accordingly, the distal bellows 915 may apply a proximal force to the distal portion 914 when the distal portion advances in a distal direction (e.g., when the distal portion is in the second position shown in FIG. 8B) to return the distal portion and the impactor 940 to a more proximal position (e.g., the first position shown in FIG. 8A). In other examples, the distal portion 914 and the proximal portion 912 of the hollow tubular body may be elastically connected, e.g., by way of an elastomer. The elastic material properties of the elastic connection may create a spring-like force that allows the impactor to advance in a distal direction and then applies a proximal force to return the distal portion and the impactor to a more proximal position. In some examples, the elastic connection comprises a region of elastic material (e.g., an elastomer) between the distal portion 914 and the proximal portion 912 of the hollow tubular body. The elastic material may be, for instance, an elastic polymeric material, a rubber, or some other elastomer that permits distal movement and a restorative force of the distal portion 914 relative to the proximal portion 912.

As mentioned above, a distal end of an enclosure 930 of a catheter may be sealed to a region of the impactor, and the enclosure may be configured to change in length in conjunction with the distal-proximal movement of the impactor. Accordingly, the enclosure 930 may include features that allow the enclosure to expand and contract in length in the distal-proximal direction responsive to the distal and proximal movement of the impactor. Such features may be included in a region of the enclosure, such as a proximal region of the enclosure or a distal region of the enclosure.

FIGS. 9B-9C illustrate various features that can be included in an enclosure 930 of a catheter that allow the enclosure to extend in conjunction with the distal advancement of the impactor and allow the enclosure to return to a non-extended state when the impactor returns in the proximal direction. For instance, FIG. 9B illustrates exemplary proximal bellows 935 that can be included in a portion (e.g., a proximal portion) of an enclosure 930 of a catheter. The proximal bellows 935 may be formed integrally form the material of the enclosure 930 (e.g., by folding the material of the enclosure one or more times into an accordion-like shape). The proximal bellows 935 may be configured to increase a length of the enclosure 930 responsive to the distal advancement of the impactor. FIG. 9C illustrates an exemplary pleated region 937 (e.g., a region of excess material that is optionally folded into a second layer of the material) that can be included in a region (e.g., a proximal region) of an enclosure 930. The pleated region may be formed integrally from the material of the enclosure 930 (e.g., by pleating the material of the enclosure one or more times to form one or more layers of material). The pleated region 935 may be similarly configured to increase a length of the enclosure 930 responsive to the distal advancement of the impactor 940 (e.g., by unfolding the second layer of the material of the pleated region 937 to increase the length of the enclosure 930).

Figure 10:
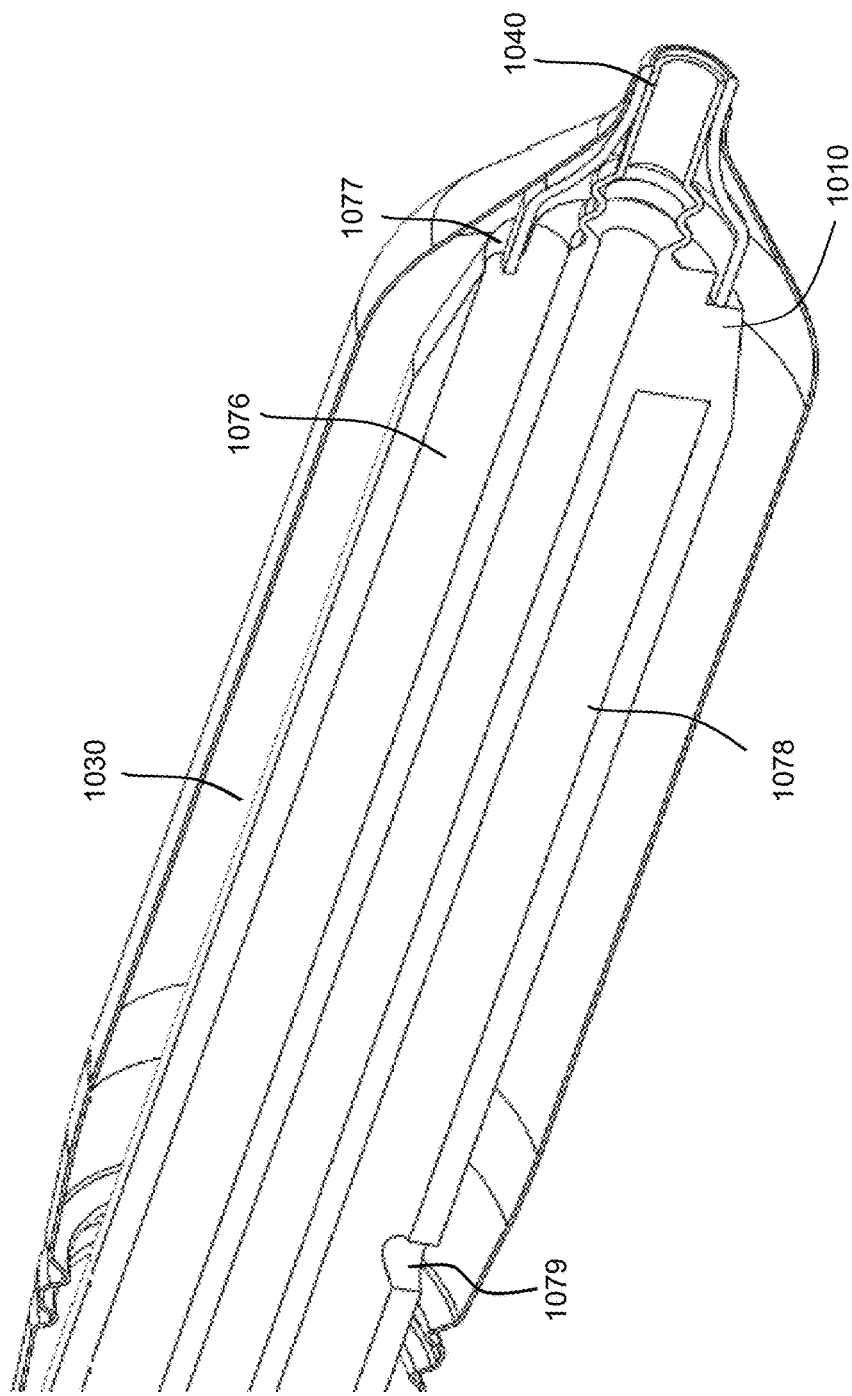
FIG. 10 illustrates a cross sectional perspective view of the distal end of an exemplary catheter showing the fluid lumens of the catheter, according to one or more examples of the present disclosure.

As mentioned above, the enclosure 930 can be filled with a fluid, optionally such that the enclosure inflates. In some examples, the fluid is a conductive fluid, e.g. a saline solution, that allows current to flow across a spark gap between spaced electrodes located inside the enclosure when a voltage is applied across the electrodes. In some examples, the fluid is continuously flowed across the emitters during a shock wave treatment, for instance, to disperse heat and to remove gas bubbles and debris produced by the generation of shock waves at the emitters. FIG. 10 illustrates a cross sectional perspective view of the distal end of an exemplary catheter 1000, showing two fluid lumens 1076, 1078 extending axially through a hollow tubular body 1010 of the catheter and configured for flowing fluid through an enclosure 1030 of the catheter. For instance, in one or more examples, the hollow tubular body 1010 includes a first fluid lumen 1076 for flowing conductive fluid into the enclosure, and a second fluid lumen 1078 for flowing conductive fluid out of the enclosure. The catheter 1000 of FIG. 10 may be any of the catheters 10, 200, 300, 400, 500, 600, 700, or 800 described above with respect to FIGS. 1-8B or any of the catheters described elsewhere in the disclosure.

Each of the fluid lumens 1076, 1078 may further include a port (e.g., an inlet or an outlet) for flowing fluid into and/or out of the enclosure 230. For instance, the first fluid lumen 1076 may include an outlet 1077 disposed in a region of the hollow tubular body 1010 and connecting the first fluid lumen with the volume of the enclosure 1030, and the second fluid lumen 1078 man include an inlet 1079 disposed in a region of the hollow tubular body and connecting the second fluid lumen with the volume of the enclosure. In some examples, the fluid outlet 1077 is disposed in a distal end of the hollow tubular body 1010 proximate to the impactor 1040 and distal to one or more proximal emitters (not shown) disposed on the hollow tubular body. In some examples, the fluid inlet 1077 is disposed in a proximal region of the hollow tubular body 1010 proximal to one or more proximal emitters disposed on the hollow tubular body. However, in other examples the fluid outlet 1077 is disposed proximal to the proximal emitters and the fluid inlet 1079 is disposed distal to the proximal emitters and near a distal tip of the hollow tubular body 1010.

Figure 11:
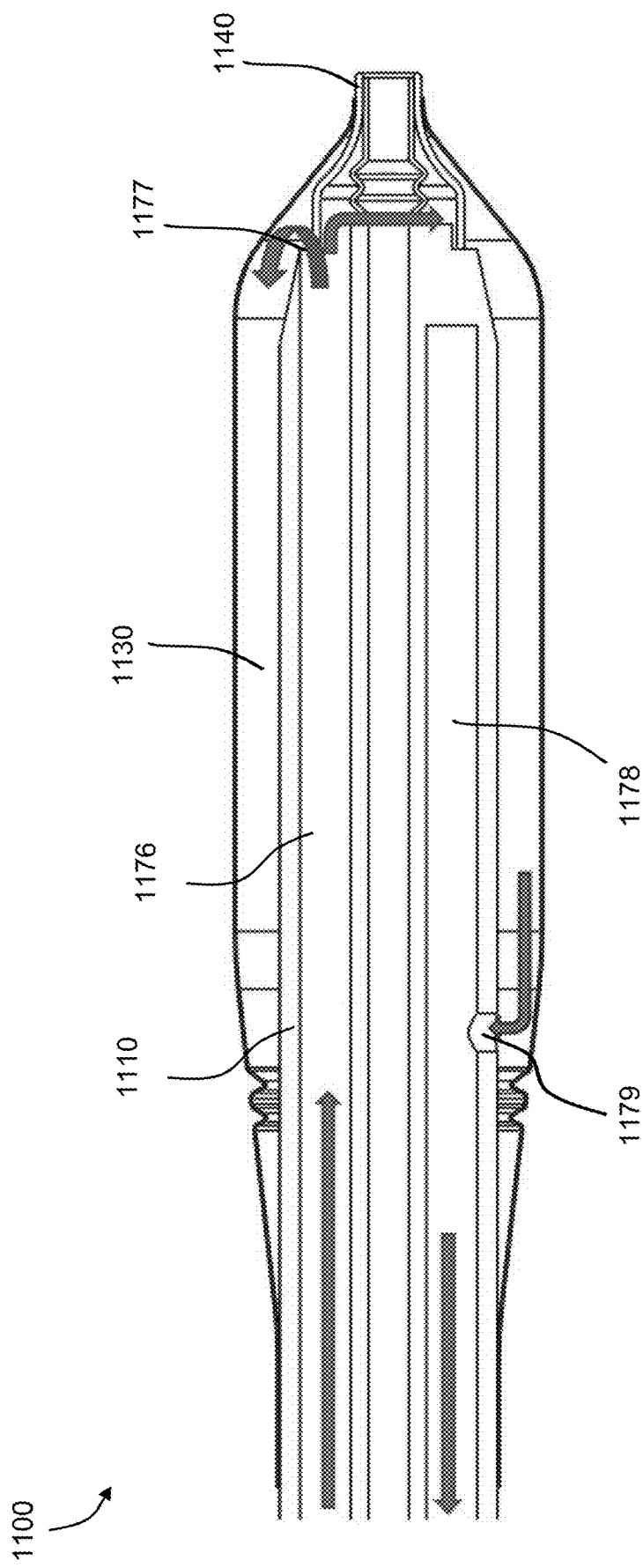
FIG. 11 illustrates a cross sectional view of the distal end of an exemplary catheter showing an exemplary path of fluid flow through an enclosure of the catheter, according to one or more examples of the present disclosure.

The outlet 1077 and inlet 1079 of the fluid lumens 1076, 1078 may be positioned such that fluid flowed through the enclosure 1030 via the fluid lumens flows across one or more of the emitters (e.g., flows across one or more spark gaps associated with one or more of the proximal emitters and/or the distal emitter). FIG. 11 illustrates a cross sectional view of the distal end of an exemplary catheter 1100, which may be any of the catheters described herein, showing an exemplary path of fluid flow through an enclosure 1130 of the catheter. For instance, fluid may be flowed through the first fluid lumen 1176 and into the enclosure 1130 through the outlet 1177 in the hollow tubular body 1110. The fluid may then flow across one or more of the distal emitter (e.g., a distal emitter formed at least partially by the impactor 1140) and/or the proximal emitters (not shown). In some examples, the path of fluid flow between the outlet 1177 and the inlet 1179 is across at least a portion of the conductive portions of the impactor 1140. In further examples, the path of fluid flow between the outlet 1177 and the inlet 1179 is across one or more conductive portions of the proximal emitters. The fluid may then flow out of the enclosure 1130 through an inlet 1179 disposed in the hollow tubular body 1110 and out through the second fluid lumen 1178.

Figure 12:
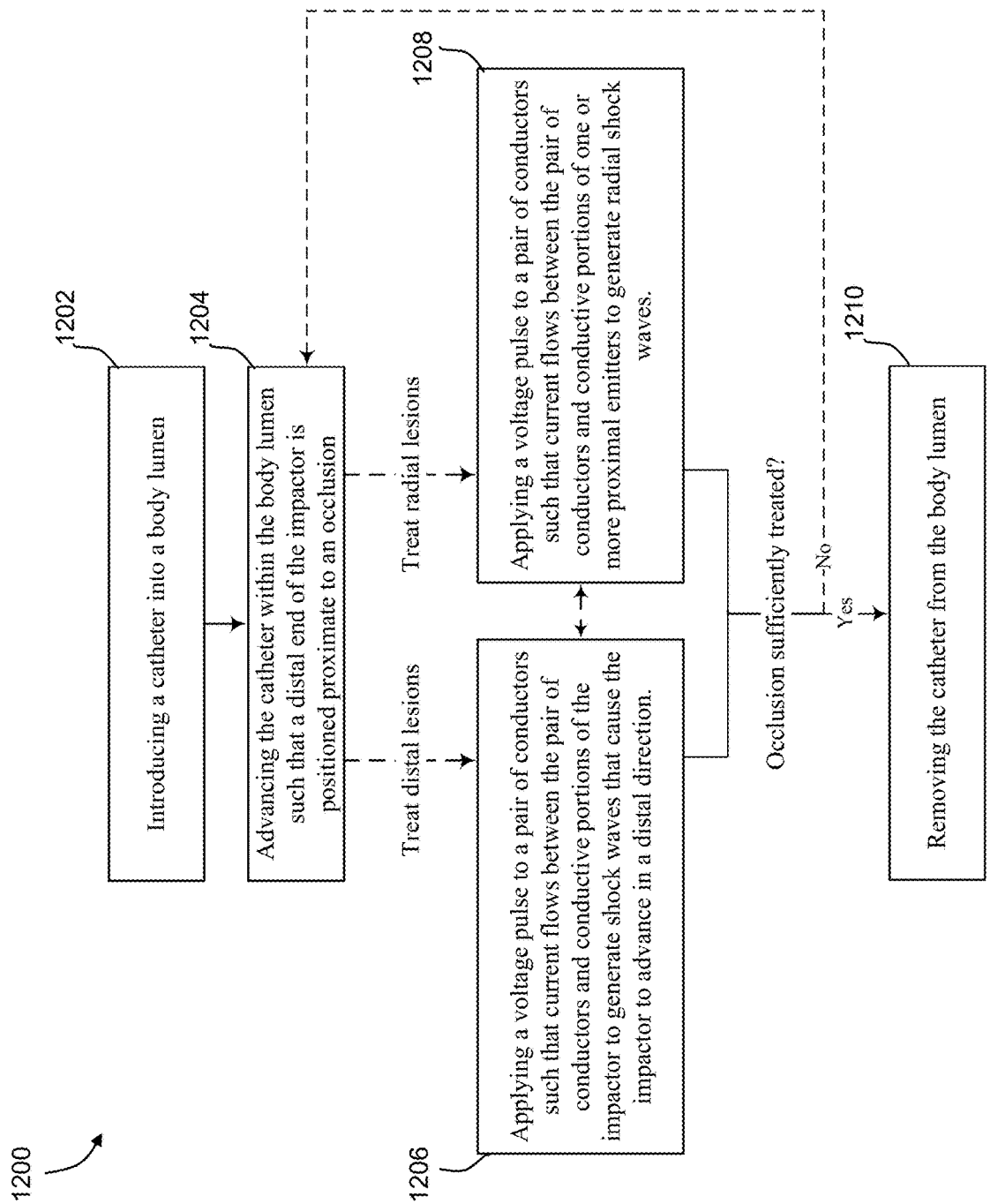
FIG. 12 illustrates a flowchart of an exemplary method of treating an occlusion in a body lumen using a catheter, according to one or more examples of the present disclosure.

FIG. 12 illustrates an exemplary method 1200 of treating an occlusion in a body lumen using a catheter, such as any of the catheters 10, 200, 300, 400, 500, 600, 700, 800, 1000, or 1100 shown in FIGS. 1-11 and described herein. In some examples, the method 1200 includes a step 1202, wherein step 1202 includes introducing a catheter into a body lumen. In some examples, introducing the catheter into the body lumen includes advancing a guide wire from an entry site on a patient (e.g., an artery in the groin area of the leg) to the target region of a vessel (e.g., a region having calcified plaques that need to be broken up), and advancing the catheter into the body lumen over the guide wire.

In some examples, the method 1200 includes a step 1204, wherein step 1202 includes advancing the catheter within the body lumen such that a distal end of the impactor is positioned proximate to an occlusion. The location of the catheter (and/or emitters of the catheter) may be determined by x-ray imaging and/or fluoroscopy. In some examples, advancing the catheter through the body lumen includes advancing the catheter until a distal tip of the catheter and/or a distal end of the impactor is proximate to or contacting an occlusion. In some examples, the enclosure of the catheter is in a collapsed or folded state when the catheter is inserted and advanced through the body lumen. In some examples, when the catheter is positioned proximate to the occlusion, the enclosure is inflated with a conductive fluid (e.g., saline and/or saline mixed with an image contrast agent) until the enclosure contacts the walls of the body lumen and/or the occlusion.

One the catheter is positioned proximate to an occlusion, energy can be applied to the catheter to generate shock waves to treat the occlusion. In some examples, the method 1200 includes a step 1206, wherein step 1202 includes applying a voltage pulse to a pair of conductors such that current flows between the pair of conductors and conductive portions of the impactor to generate shock waves that cause the impactor to advance in a distal direction. Repeated generation of shock waves causes the impactor to oscillate and produces a "jackhammer effect" that chisels away at the occlusion and creates a small tunnel in the occlusion allowing the catheter to be advanced forward in the body lumen. Once the catheter tip enters the tunnel, radial shock waves (e.g., shock waves generated at one or more proximal emitters) may be used to crack calcium in the lumen wall and the shock wave treatment can be continued. In some examples, the catheter includes one or more distal emitters and one or more proximal emitters. In some examples, a distal emitter can be used to drive the impactor forward in a distal direction to apply a mechanical force to an occlusion, while proximal emitters can be used to treat areas of a body lumen proximal to the occlusion and surrounding the catheter. Accordingly, in some examples, the method 1200 includes a step 1208, wherein step 1208 includes applying a voltage pulse to a pair of conductors such that current flows between the pair of conductors and conductive portions or one or more proximal emitters to generate radial shock waves.

The distal emitter and the proximal emitters may be wired separately to a power source, such that an operator (e.g., a physician) may selectively generate shock waves at one or more of the distal emitter and the proximal emitter(s). In such examples, an operator may generate shock waves first at a distal emitter to cause the impactor to deliver a mechanical force to a distal occlusion, and subsequently at the proximal emitter(s) to treat more proximal regions of the body lumen (or vice versa). In some examples, the treatment may be conducted in one or more stages or phases. For instance, a physician may initially position the catheter near a first portion of an occlusion and generate shock waves to treat the first portion of the occlusion. If the occlusion is not cleared by a first round of shock waves, the physician may reposition the catheter to move it further along the length of the body lumen and additional shock waves can be generated to treat a second portion of the occlusion. Once the occlusion has been sufficiently treated, the enclosure may be inflated further or deflated, and the catheter and guide wire may be withdrawn from the patient. In some examples, the method 1200 includes a step 1210, wherein step 1210 includes removing the catheter from the body lumen.

Although the electrode assemblies and catheter devices described herein have been discussed primarily in the context of treating coronary occlusions, such as CTOs and lesions in vasculature, the electrode assemblies and catheters herein can be used for a variety of occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject disclosure.

It should be noted that the elements and features of the exemplary electrode assemblies and catheters discussed and illustrated throughout this specification and drawings may be rearranged, recombined, and modified without departing from the present disclosure. For instance, while this specification and drawings describe and illustrate catheters having several example balloon designs, the present disclosure is intended to include catheters having a variety of balloon configurations. The number, placement, and spacing of the electrode pairs of the shock wave generators can be modified without departing from the subject disclosure. Further, the number, placement, and spacing of balloons of catheters can be modified without departing from the subject disclosure.

It should be understood that the foregoing is only illustrative of the principles of the disclosure, and that various modifications, alterations and combinations can be made by those skilled in the art without departing from the scope and spirit of the disclosure. Any of the variations of the various catheters disclosed herein can include features described by any other catheters or combination of catheters herein. Furthermore, any of the methods can be used with any of the catheters disclosed. Accordingly, it is not intended that the disclosure be limited, except as by the appended claims.

The invention claimed is:

1. A catheter for treating an occlusion in a body lumen, the catheter comprising:
    a hollow tubular body comprising a distal portion configured to move relative to a proximal portion of the hollow tubular body;
    a conductor configured to receive a voltage pulse from a voltage source; and
    an impactor mounted on, and at least partially encircling, the distal portion of the hollow tubular body, the impactor comprising a conductive portion adjacent to a distal end of the conductor;
    wherein, when a voltage pulse is applied to the conductor, current flows across a gap between the conductor and the conductive portion to generate one or more shock waves that cause the impactor to move in a distal direction.

2. The catheter of claim 1, wherein, when the impactor moves in the distal direction, the distal portion of the hollow tubular body moves in conjunction with the impactor.

3. The catheter of claim 2, wherein the impactor and the distal portion move in the distal direction with respect to the proximal portion of the hollow tubular body.

4. The catheter of claim 1, wherein the distal portion is elastically coupled to the proximal portion.

5. The catheter of claim 1, wherein the distal portion comprises bellows that increase a length of the distal portion when the impactor moves in the distal direction.

6. The catheter of claim 1, wherein the impactor moves in a distal direction less than 0.5 mm with respect to the proximal portion of the hollow tubular body.

7. The catheter of claim 1, wherein the impactor comprises a conductive metal sheath.

8. The catheter of claim 1, wherein the impactor tapers from a proximal end of the impactor to a distal end of the impactor.

9. The catheter of claim 1, wherein the conductive portion of the impactor comprises a first conductive portion and a second conductive portion.

10. The catheter of claim 9, wherein the first conductive portion comprises a first cut-out in a proximal edge of the impactor, and wherein the second conductive portion comprises a second cut-out in the proximal edge of the impactor.

11. The catheter of claim 1, further comprising an enclosure surrounding at least a portion of the hollow tubular body.

12. The catheter of claim 11, wherein a proximal end of the enclosure is sealed to the proximal portion of the hollow tubular body.

13. The catheter of claim 11, wherein a distal end of the enclosure is sealed to the impactor.

14. The catheter of claim 13, wherein the enclosure extends in length in conjunction with the movement of the impactor.

15. The catheter of claim 14, wherein the enclosure comprises bellows that increase a length of the enclosure when the impactor moves in the distal direction.

16. The catheter of claim 11, wherein the hollow tubular body comprises:
a first fluid lumen for flowing conductive fluid into the enclosure, the first fluid lumen having an outlet; and
a second fluid lumen for flowing conductive fluid out of the enclosure, the second fluid lumen having an inlet;
wherein a path of fluid flow between the outlet and the inlet is across at least a portion of the conductive portion of the impactor.

17. The catheter of claim 1, wherein the conductor forms a first electrode of an electrode pair, and wherein a second electrode of the electrode pair is formed by the conductive portion of the impactor.

18. The catheter of claim 1, wherein the conductor comprises a first pair of conductors.

19. The catheter of claim 18, wherein the conductive portion of the impactor is a first conductive portion, and wherein the first pair of conductors comprises:
a first insulated wire extending along a length of the hollow tubular body, the first insulated wire having an exposed distal tip spaced apart from the first conductive portion of the impactor at a first spark gap; and
a second insulated wire extending along the length of the hollow tubular body, the second insulated wire having an exposed distal tip spaced apart from a second conductive portion of the impactor at a second spark gap;
wherein, when a voltage pulse is applied across the first insulated wire and the second insulated wire, a current is configured to flow from the exposed distal tip of the first insulated wire to the first conductive portion across the first spark gap to generate a first shock wave, and wherein the current is further configured to flow from the second conductive portion to the exposed distal tip of the second insulated wire across the second spark gap to generate a second shock wave.

20. The catheter of claim 18, further comprising a second pair of conductors configured to receive a voltage pulse from a voltage source, wherein, when a voltage pulse is applied to the second pair of conductors, current flows between the second pair of conductors and one or more proximal emitters to generate shock waves at the one or more proximal emitters.

21. The catheter of claim 20, further comprising a power source, wherein the power source is configured for selectively applying voltage pulses across either the first pair of conductors or the second pair of conductors.

22. A catheter for treating an occlusion in a body lumen, the catheter comprising:
a tubular body having a distal end;
a distal portion elastically connected to the distal end of the tubular body;
an impactor connected to, and at least partially encircling, the distal portion and separated by a space from the distal end of the tubular body;
a distal shock wave emitter located adjacent to the space; and
an enclosure at least partially surrounding each of the distal end of the tubular body, the elastic distal portion, the impactor, and the distal shock wave emitter,
wherein the impactor is configured to move in response to a shock wave generated from the distal shock wave emitter such that a length of the space in the proximal-distal direction increases by between 0.05 mm and 0.6 mm.

23. A catheter for treating an occlusion in a body lumen, the catheter comprising:
a tubular body comprising a distal end;
a distal portion elastically connected to the distal end of the tubular body;
an impactor connected to, and at least partially encircling, the distal portion and configured to move in a distal-proximal direction; and
a shock wave emitter located on or proximate the tubular body; and
an enclosure surrounding the shock wave emitter and including a proximal region, the proximal region configured to expand in the distal-proximal direction in conjunction with distal movement of the impactor and further configured to contract in the distal-proximal direction in conjunction with proximal movement of the impactor.

24. The catheter of claim 23, wherein the proximal region of the enclosure comprises proximal bellows.

25. The catheter of claim 23, wherein the proximal region of the enclosure comprises pleats.

26. The catheter of claim 23, wherein the proximal region is configured to expand in the distal-proximal direction responsive to shock waves generated at the shock wave emitter.

* * * * *